United States Patent
Kaelin et al.

(10) Patent No.: US 11,340,216 B2
(45) Date of Patent: May 24, 2022

(54) METHODS AND COMPOSITIONS FOR THE POSITIVE SELECTION OF PROTEIN DESTABILIZERS

(71) Applicant: Dana-Farber Cancer Institute, Inc., Boston, MA (US)

(72) Inventors: William G. Kaelin, Boston, MA (US); Vidyasagar Koduri, Brookline, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 16/332,921

(22) PCT Filed: Sep. 13, 2017

(86) PCT No.: PCT/US2017/051371
§ 371 (c)(1),
(2) Date: Mar. 13, 2019

(87) PCT Pub. No.: WO2018/053006
PCT Pub. Date: Mar. 22, 2018

(65) Prior Publication Data
US 2019/0234934 A1  Aug. 1, 2019

Related U.S. Application Data

(60) Provisional application No. 62/394,023, filed on Sep. 13, 2016.

(51) Int. Cl.
| | | |
|---|---|---|
| *G01N 33/50* | (2006.01) |
| *C12Q 1/37* | (2006.01) |
| *C12Q 1/48* | (2006.01) |
| *C07K 14/00* | (2006.01) |
| *C07K 14/435* | (2006.01) |
| *C12N 9/12* | (2006.01) |
| *C12N 9/64* | (2006.01) |

(52) U.S. Cl.
CPC .......... *G01N 33/502* (2013.01); *C07K 14/00* (2013.01); *C07K 14/435* (2013.01); *C12N 9/1211* (2013.01); *C12N 9/1229* (2013.01); *C12N 9/1241* (2013.01); *C12N 9/6472* (2013.01); *C12Q 1/37* (2013.01); *C12Q 1/485* (2013.01); *C07K 2319/95* (2013.01); *G01N 2500/10* (2013.01); *G01N 2510/00* (2013.01)

(58) Field of Classification Search
CPC .... G01N 33/502; C07K 14/00; C07K 14/435; C12N 9/1211
See application file for complete search history.

(56) References Cited

U.S. PATENT DOCUMENTS

| | | |
|---|---|---|
| 5,187,287 A | 2/1993 | Shih |
| 5,847,102 A | 12/1998 | Singh et al. |
| 6,063,985 A | 5/2000 | Chua et al. |
| 6,171,821 B1 | 1/2001 | Korneluk et al. |
| 8,809,017 B2 | 8/2014 | Yang et al. |
| 2004/0214223 A1 | 10/2004 | Cao et al. |
| 2007/0248543 A1 | 10/2007 | Gojkovic |
| 2010/0041054 A1 | 2/2010 | Mack |
| 2010/0099096 A1 | 4/2010 | Elledge et al. |
| 2011/0052539 A1 | 3/2011 | Stojdl et al. |
| 2011/0191873 A1 | 8/2011 | Stack et al. |
| 2012/0301919 A1 | 11/2012 | Yang et al. |
| 2013/0315885 A1 | 11/2013 | Narain et al. |
| 2014/0162282 A1 | 6/2014 | Schafer et al. |
| 2017/0292959 A1 | 10/2017 | Kaelin et al. |
| 2017/0306385 A1* | 10/2017 | Kaelin ................... C12Q 1/02 |

FOREIGN PATENT DOCUMENTS

| | | |
|---|---|---|
| WO | WO 2001/009357 A2 | 2/2001 |
| WO | WO 2002/044427 A2 | 6/2002 |
| WO | WO 2002/064802 A2 | 8/2002 |
| WO | WO 2008/106087 A1 | 9/2008 |
| WO | WO 2013/130482 A1 | 9/2013 |
| WO | WO 2016/057897 A1 | 4/2016 |
| WO | WO 2016/057903 A1 | 4/2016 |
| WO | WO 2018/053006 A1 | 3/2018 |

OTHER PUBLICATIONS

Ernst-Jan Geutjes. Deoxycytidine kinase is overexpressed in poor outcome breast cancer and determines responsiveness to nucleoside analogs. Breast Cancer Res Treat (2012) 131:809-818. (Year: 2012).*
PCT/US2015/054893, Dec. 15, 2015, Invitation to Pay Additional Fees.
PCT/US2015/054893, Feb. 8, 2016, International Search Report and Written Opinion.
PCT/US2015/054893, Apr. 20, 2017, International Preliminary Report on Patentability.
PCT/US2015/054914, Jan. 11, 2016, International Search Report and Written Opinion.
PCT/US2015/054914, Apr. 20, 2017, International Preliminary Report on Patentability.
EP 15848994.8, Feb. 16, 2018, Extended European Search Report.
EP 15848217.4, Feb. 16, 2018, Extended European Search Report.
PCT/US2017/051371, Nov. 29, 2017, International Search Report and Written Opinion.
PCT/US2017/051371, Mar. 28, 2019, International Preliminary Report on Patentability.
Attal et al., The RU5 ('R') region from human leukaemia viruses (HTLV-1) contains an internal ribosome entry site (IRES)-like sequence. FEBS Lett. Sep. 2, 1996; 392(3):220-4.
Belsham et al., Dual initiation sites of protein synthesis on foot-and-mouth disease virus RNA are selected following internal entry and scanning of ribosomes in vivo. EMBO J. Mar. 1992; 11(3):1105-10.

(Continued)

*Primary Examiner* — Kagnew H Gebreyesus
(74) *Attorney, Agent, or Firm* — Wolf, Greenfield & Sacks, P.C.

(57) ABSTRACT

The present application relates, in some aspects, to the development of an assay that uses cell survival and/or cell viability as a phenotypic identifier to positively select for agents that destabilize a protein of interest.

18 Claims, 31 Drawing Sheets

(56) References Cited

OTHER PUBLICATIONS

Campanero et al., Regulation of E2F through ubiquitin-proteasome-dependent degradation: stabilization by the pRB tumor suppressor protein. Proc Natl Acad Sci U S A. Mar. 18, 1997;94(6):2221-6.
De Gregorio et al., Translation driven by an eIF4G core domain in vivo. EMBO J. Sep. 1, 1999;18(17):4865-74.
Derrington et al., Retroviral vectors for the expression of two genes in human multipotent neural precursors and their differentiated neuronal and glial progeny. Hum Gene Ther. May 1, 1999;10(7):1129-38.
Ferreirós-Vidal et al., Genome-wide identification of Ikaros targets elucidates its contribution to mouse B-cell lineage specification and pre-B-cell differentiation. Blood. Mar. 7, 2013;121(10):1769-82. doi:10.1182/blood-2012-08-450114. Epub Jan. 9, 2013.
Hsieh et al., Improved gene expression by a modified bicistronic retroviral vector. Biochem Biophys Res Commun. Sep. 25, 1995;214(3):910-7.
Ishii et al., A new internal ribosomal entry site 5' boundary is required for poliovirus translation initiation in a mouse system. J Virol. Mar. 1998; 72(3):2398-405.
Ito et al., Identification of a primary target of thalidomide teratogenicity. Science. Mar. 12, 2010;327(5971):1345-50. doi: 10.1126/science. 1177319.
Kim et al., Construction of a bifunctional mRNA in the mouse by using the internal ribosomal entry site of the encephalomyocarditis virus. Mol Cell Biol. Aug. 1992; 12(8):3636-43.
Lemon et al., Internal ribosome entry sites within the RNA genomes of hepatitis C virus and other flaviviruses. Semin Virol. 1997; 8:274-288.
Lopez-Girona et al., Cereblon is a direct protein target for immunomodulatory and antiproliferative activities of lenalidomide and pomalidomide. Leukemia. Nov. 2012;26(11):2326-35. doi:10. 1038/leu.2012.119. Epub May 3, 2012. Erratum in: Leukemia. Nov. 2012;26(11):2445.
Lu et al., Online supplementary material for : The myeloma drug lenalidomide promotes the cereblon-dependent destruction of Ikaros proteins. Science. Nov. 28, 2013: pp. 1-36.
Lu et al., The myeloma drug lenalidomide promotes the cereblon-dependent destruction of Ikaros proteins. Science. Jan. 17, 2014;343(6168):305-9. doi:10.1126/science.1244917. Epub Nov. 29, 2013.
Martiniani et al., Biological activity of lenalidomide and its underlying therapeutic effects in multiple myeloma. Adv Hematol. 2012;2012:842945. doi: 10.1155/2012/842945. Epub Aug. 2, 2012.
Monticelli et al., Negative regulators take center stage. Nat Immunol. Jul. 19, 2012;13(8):719-20. doi: 10.1038/ni.2377.
Ngoi et al., Exploiting internal ribosome entry sites in gene therapy vector design. Curr Gene Ther. Mar. 2004;4(1):15-31.

Oh et al., Homeotic gene Antennapedia mRNA contains 5'-noncoding sequences that confer translational initiation by internal ribosome binding. Genes Dev. Sep. 1992; 6(9):1643-53.
Ohlmann et al., An Internal Ribosome Entry Segment Promotes Translation of the Simian Immunodeficiency Virus Genomic RNA. J. Biol. Chem. 2000; 275:11899-906. doi:10.1074/jbc.275.16. 11899.
Owens et al., Identification of two short internal ribosome entry sites selected from libraries of random oligonucleotides. Proc Natl Acad Sci U S A. Feb. 13, 2001; 98(4):1471-6.
Pfutzner, Retroviral bicistronic vectors. Drug News Perspect. Nov. 2008;21(9):473-80. doi: 10.1358/dnp.2008.21.9.1290817.
Pöyry et al., Construction of regulatable picornavirus IRESes as a test of current models of the mechanism of internal translation initiation. RNA. May 2001; 7(5):647-60.
Safran et al., Mouse model for noninvasive imaging of HIF prolyl hydroxylase activity: assessment of an oral agent that stimulates erythropoietin production. Proc Natl Acad Sci U S A. Jan. 3, 2006;103(1):105-10. Epub Dec. 22, 2005.
Sato et al., Engineered human tmpk/AZT as a novel enzyme/prodrug axis for suicide gene therapy. Mol Ther. May 2007; 15(5):962-70. Epub Mar. 20, 2007.
Shiroki et al., Host range phenotype induced by mutations in the internal ribosomal entry site of poliovirus RNA. J Virol. Jan. 1997; 71(1): 1-8.
Stoneley et al., Analysis of the c-myc IRES; a potential role for cell-type specific trans-acting factors and the nuclear compartment. Nucleic Acids Res. Feb. 1, 2000; 28(3):687-94.
Terpos et al., Pomalidomide: a novel drug to treat relapsed and refractory multiple myeloma. Onco Targets Ther. May 10, 2013;6:531-8. doi: 10.2147/OTT.S34498. Print 2013.
Tsukiyama-Kohara et al., Internal ribosome entry site within hepatitis C virus RNA. J Virol. Mar. 1992; 66(3):1476-83.
Venkatesan et al., Novel fluorescence-based screen to identify small synthetic internal ribosome entry site elements. Mol Cell Biol. Apr. 2001; 21(8):2826-37.
Wiederschain et al., Single-vector inducible lentiviral RNAi system for oncology target validation. Cell Cycle. Feb. 1, 2009;8(3):498-504. Epub Feb. 25, 2009.
Wong et al., Improved co-expression of multiple genes in vectors containing internal ribosome entry sites (IRESes) from human genes. Gene Ther. Mar. 2002;9(5):337-44.
Yen et al., Global protein stability profiling in mammalian cells. Science. Nov. 7, 2008;322(5903):918-23. doi:10.1126/science. 1160489.
Zhang et al., Bioluminescent imaging of Cdk2 inhibition in vivo. Nat Med. Jun. 2004;10(6):643-8. Epub May 2, 2004.
Zhang et al., Lenalidomide efficacy in activated B-cell-like subtype diffuse large B-cell lymphoma is dependent upon IRF4 and cereblon expression. Br J Haematol. Feb. 2013;160(4):487-502. doi: 10.1111/bjh.12172. Epub Dec. 18, 2012.
Zhu et al., Molecular mechanism of action of immune-modulatory drugs thalidomide, lenalidomide and pomalidomide in multiple myeloma. Leuk Lymphoma. Apr. 2013;54(4):683-7. doi: 10.3109/10428194.2012.728597. Epub Sep. 28, 2012.

* cited by examiner

METHODS AND COMPOSITIONS FOR THE POSITIVE SELECTION OF PROTEIN DESTABILIZERS

RELATED APPLICATIONS

This application is a national stage filing under 35 U.S.C. § 371 of International PCT Application No. PCT/US2017/051371, filed Sep. 13, 2017, which claims priority under 35 U.S.C. § 119(e) to U.S. Provisional Patent Application No. 62/394,023, filed Sep. 13, 2016, each of which is hereby incorporated by reference in its entirety.

FEDERALLY SPONSORED RESEARCH

This invention was made with government support under Grant Nos. R01 CA068490 and R01 CA076120 awarded by the National Institutes of Health. The government has certain rights in the invention.

BACKGROUND

Reporter assays have been used routinely in the pharmaceutical and biotechnology industries to identify lead compounds that affect protein function. In the last decade, the chemist's ability to synthesize large numbers of chemical compounds in a short amount of time through techniques such as combinatorial chemistry has greatly increased, and often, thousands to millions of compounds need to be screened to identify those having a desired effect on a protein of interest. Typically, reporter assays measure the activities of a protein of interest (POI) in the presence of a test agent to evaluate the ability of the test agent to affect the function of the POI.

SUMMARY

In screening for an agent that downregulates a POI, most previous assays were "down" assays, meaning that a hit is identified by a decrease in a detectable signal corresponding to the downregulated POI, such as a decrease in a reporter protein signal. Such down assays can be a source of artifacts, as there are typically more spurious or trivial ways to downregulate than upregulate in biological assays. Assays of the present invention are "up" assays, meaning that a hit is identified by a positive indicator, such as cell growth and/or survival.

The present disclosure relates, in some aspects, to the development of up assays in which cell survival may be used to positively select for agents that destabilize a POI. In various aspects, the disclosure provides a description of compositions and methods that utilize fusion constructs having a cytotoxic element fused to a POI, whereby degradation of the fusion construct promotes cell survival and/or cell viability.

Accordingly, in some aspects, the disclosure provides a method of identifying a test agent that destabilizes a POI, the method comprising: providing cells expressing a recombinant fusion protein comprising a POI and an enzyme, wherein the enzyme converts an exogenous substrate that is not toxic to the cells into a product that is toxic to the cells; contacting a first portion of the cells with a test agent; culturing the first portion of the cells in the presence of the first exogenous substrate; culturing, separately from the first portion of cells, a second portion of the cells in the presence of the exogenous substrate, wherein the second portion of the cells is not contacted with the test agent; and determining a level of cell survival in each of the cultured portions, wherein a greater level of survival (e.g., cell survival) in the first portion compared to the second portion indicates that the test agent destabilizes the POI.

In some embodiments, the POI is an oncoprotein. In some embodiments, the oncoprotein is selected from the group consisting of MYC, Ikaros family zinc finger protein 1 (IKZF1), Ikaros family zinc finger protein 3 (IKZF3), Interferon regulatory factor 4 (IRF4), mutant p53, N-Ras, K-Ras, c-Fos, c-Jun, and estrogen receptor (ER). In some embodiments, the POI is a protein associated with neurodegeneration, e.g., a protein whose accumulation is associated with neurodegeneration. In some embodiments, the POI is a prion. In some embodiments, the POI is an amyloid protein.

In some embodiments, the enzyme is selected from the group consisting of deoxycytidine kinase, thymidylate kinase, thymidine kinase-guanylate kinase fusion, and FKBP-Caspase9 fusion.

In some embodiments, the exogenous substrate is a synthetic compound. In some embodiments, the synthetic compound is a nucleoside analog. In some embodiments, the nucleoside analog is selected from the group consisting of bromovinyl-deoxyuridine, azidothymidine (AZT), and Ganciclovir. In some embodiments, the synthetic compound is AP1903. In some embodiments, the test agent is selected from the group consisting of a small organic molecule, an amino acid, a protein, a nucleoside, a nucleotide, a nucleic acid, or an analog or derivative thereof. In some embodiments, the test agent is an immunomodulatory drug (IMiD). In some embodiments, the IMiD is selected from the group consisting of thalidomide, lenalidomide, and pomalidomide. In some embodiments, the test agent is an estrogen receptor antagonist. In some embodiments, the estrogen receptor antagonist is Fulvestrant.

In some embodiments, the cells further express a reporter protein. In some embodiments, the reporter protein is a fluorescent protein or a bioluminescent protein. In some embodiments, the fluorescent protein is selected from the group consisting of green fluorescent protein, tdTomato, and red fluorescent protein. In some embodiments, the bioluminescent protein is selected from the group consisting of renilla luciferase (RLuc) and firefly luciferase (FLuc).

In some aspects, the disclosure provides a method of identifying a test agent that destabilizes a POI, the method comprising providing cells expressing a recombinant fusion protein comprising a POI and an enzyme, wherein the enzyme converts an exogenous substrate that is not toxic to the cells into a product that is toxic to the cells; contacting the cells with a library of test agents; culturing the cells in the presence of the exogenous substrate; determining cell survival in the cultured cells, wherein survival of a cell indicates that a test agent from the library of test agents destabilizes the POI; and isolating the surviving cell. In some embodiments, the method further comprises identifying the test agent from the surviving cell.

In some embodiments, the library of test agents is selected from the group consisting of a library of nucleic acids, a library of peptides, a library of antibodies or antigen-binding fragments thereof, and a library of small organic molecules. In some embodiments, the library of nucleic acids comprises DNA, cDNA, RNA, siRNA, shRNA, miRNA, sgRNA, mRNA, or some combination thereof. In some embodiments, the library of test agents is a viral library. In some embodiments, the viral library is selected from the group consisting of a lentiviral library, a retroviral library, an adenoviral library, an adeno-associated viral library, a herpes simplex viral library, and a baculoviral library.

In some embodiments, contacting the cells with the library of agents comprises transducing the cells with the viral library.

In some embodiments, the test agent is identified by nucleic acid sequencing. In some embodiments, the test agent is identified by peptide sequencing.

In some embodiments, the cells further express a reporter protein. In some embodiments, the reporter protein is a fluorescent protein or a bioluminescent protein. In some embodiments, the fluorescent protein is selected from the group consisting of green fluorescent protein, tdTomato, and red fluorescent protein. In some embodiments, the bioluminescent protein is selected from the group consisting of renilla luciferase (RLuc) and firefly luciferase (FLuc).

In some embodiments, the test agent destabilizes the POI by degrading the POI.

In some embodiments, the test agent destabilizes the POI by degrading an mRNA molecule encoding the POI.

In some embodiments, the test agent destabilizes the POI by degrading an mRNA molecule encoding a protein that regulates the stability of the protein of interest.

In some aspects, the disclosure provides a method of identifying a test agent that destabilizes a POI, the method comprising: providing a mixture of cells comprising a first portion of cells expressing a recombinant fusion protein comprising a POI and an enzyme and a second portion of cells expressing a recombinant protein comprising the enzyme, wherein the enzyme converts an exogenous substrate that is not toxic to the cells into a product that is toxic to the cells; contacting the mixture of cells with a test agent; culturing the mixture of cells in the presence of the exogenous substrate; and determining a level of cell survival (e.g., a number of surviving cells) for each of the portions in the cultured mixture, wherein a ratio of the number of cells in the first portion to the number of cells in the second portion in the cultured mixture greater than 1 indicates that the test agent destabilizes the POI.

In some embodiments, the method further comprises: providing an aliquot of the mixture of cells that has not been contacted with the test agent; culturing the aliquot in the presence of the exogenous substrate; and determining the level of cell survival for each of the portions in the cultured aliquot, wherein a ratio of the number of cells in the first portion to the number of cells in the second portion in the cultured aliquot that is less than the ratio in the cultured mixture indicates that the test compound destabilizes the protein of interest.

In some embodiments, the first portion of cells further expresses a first reporter protein and the second portion of cells further expresses a second reporter protein, wherein the second reporter protein is different from the first reporter protein. In some embodiments, the first reporter protein and the second reporter protein are each independently a fluorescent protein or a bioluminescent protein. In some embodiments, the fluorescent protein is selected from the group consisting of green fluorescent protein, tdTomato, and red fluorescent protein. In some embodiments, the level of cell survival is determined by flow cytometry. In some embodiments, the bioluminescent protein is selected from the group consisting of renilla luciferase (RLuc) and firefly luciferase (FLuc).

In some embodiments, the ratio of the first portion to the second portion in the mixture is less than 1 prior to culturing. In some embodiments, the ratio of the first portion to the second portion is approximately 0.1, 0.01, or 0.001.

In some embodiments, the POI is an oncoprotein. In some embodiments, the oncoprotein is selected from the group consisting of MYC, Ikaros family zinc finger protein 1 (IKZF1), Ikaros family zinc finger protein 3 (IKZF3), Interferon regulatory factor 4 (IRF4), mutant p53, N-Ras, K-Ras, c-Fos, c-Jun, and estrogen receptor (ER). In some embodiments, the POI is a protein associated with neurodegeneration, e.g., a protein whose accumulation is associated with neurodegeneration. In some embodiments, the POI is a prion. In some embodiments, the POI is an amyloid protein.

In some embodiments, the enzyme is selected from the group consisting of deoxycytidine kinase, thymidylate kinase, thymidine kinase-guanylate kinase fusion, and FKBP-Caspase9 fusion.

In some embodiments, the exogenous substrate is a synthetic compound. In some embodiments, the synthetic compound is a nucleoside analog. In some embodiments, the nucleoside analog is selected from the group consisting of bromovinyl-deoxyuridine, azidothymidine (AZT), and Ganciclovir. In some embodiments, the synthetic compound is AP1903. In some embodiments, the test agent is an IMiD. In some embodiments, the IMiD is selected from the group consisting of thalidomide, lenalidomide, and pomalidomide. In some embodiments, the test agent is an estrogen receptor antagonist. In some embodiments, the estrogen receptor antagonist is Fulvestrant.

In some aspects, the disclosure provides a DNA vector comprising in operable linkage: (a) a promoter; (b) a nucleotide sequence encoding a fusion protein comprising a POI fused to a cytotoxic element (e.g., deoxycytidine kinase (dCK)); (c) an internal ribosomal entry site (IRES); and (d) a nucleotide sequence encoding a reporter protein. In some embodiments, the cytotoxic element is an enzyme. In some embodiments, the enzyme is selected from the group consisting of deoxycytidine kinase, thymidylate kinase, thymidine kinase-guanylate kinase fusion, and FKBP-Caspase9 fusion.

In some embodiments, the fusion protein comprises a linker fusing the protein of interest to the cytotoxic element (e.g., dCK). In some embodiments, the linker comprises a peptide linker. In some embodiments, the peptide linker comprises one or more iterations of the amino acid sequence Glycine-Glycine-Serine. In some embodiments, the reporter protein is a fluorescent protein or a bioluminescent protein. In some embodiments, the fluorescent protein is selected from the group consisting of green fluorescent protein, tdTomato, and red fluorescent protein. In some embodiments, the bioluminescent protein is selected from the group consisting of renilla luciferase (RLuc) and firefly luciferase (FLuc).

In some embodiments, the promoter is an inducible promoter. In some embodiments, the promoter is a eukaryotic promoter or a synthetic promoter. In some embodiments, the promoter comprises cytomegalovirus (CMV) promoter. In some embodiments, the POI is derived from an ORFeome of an organism. In some embodiments, the POI comprises an oncoprotein. In some embodiments, the oncoprotein is selected from the group consisting of MYC, Ikaros family zinc finger protein 1 (IKZF1), Ikaros family zinc finger protein 3 (IKZF3), Interferon regulatory factor 4 (IRF4), mutant p53, N-Ras, K-Ras, c-Fos, c-Jun, and estrogen receptor (ER). In some embodiments, the POI is a protein associated with neurodegeneration, e.g., a protein whose accumulation is associated with neurodegeneration. In some embodiments, the POI is a prion. In some embodiments, the POI is an amyloid protein.

In some aspects, the disclosure provides an isolated host cell comprising a DNA vector comprising in operable linkage: (a) a promoter; (b) a nucleotide sequence encoding a fusion protein comprising a POI fused to a cytotoxic element (e.g., deoxycytidine kinase (dCK)); (c) an internal ribosomal entry site (IRES); and (d) a nucleotide sequence encoding a reporter protein. In some embodiments, the isolated host cell is a bacterial cell, a yeast cell, a plant cell, an insect cell, or a mammalian cell. In some embodiments, the cytotoxic element is an enzyme. In some embodiments, the enzyme is selected from the group consisting of deoxycytidine kinase, thymidylate kinase, thymidine kinase-guanylate kinase fusion, and FKBP-Caspase9 fusion.

In some embodiments, the fusion protein comprises a linker fusing the protein of interest to the cytotoxic element (e.g., dCK). In some embodiments, the linker comprises a peptide linker. In some embodiments, the peptide linker comprises one or more iterations of the amino acid sequence Glycine-Glycine-Serine. In some embodiments, the reporter protein is a fluorescent protein or a bioluminescent protein. In some embodiments, the fluorescent protein is selected from the group consisting of green fluorescent protein, tdTomato, and red fluorescent protein. In some embodiments, the bioluminescent protein is selected from the group consisting of renilla luciferase (RLuc) and firefly luciferase (FLuc).

In some embodiments, the promoter is an inducible promoter. In some embodiments, the promoter is a eukaryotic promoter or a synthetic promoter. In some embodiments, the promoter comprises cytomegalovirus (CMV) promoter. In some embodiments, the open reading frame is derived from an ORFeome of an organism. In some embodiments, the open reading frame encodes an oncoprotein. In some embodiments, the oncoprotein is selected from the group consisting of MYC, Ikaros family zinc finger protein 1 (IKZF1), Ikaros family zinc finger protein 3 (IKZF3), Interferon regulatory factor 4 (IRF4), mutant p53, N-Ras, K-Ras, c-Fos, c-Jun, and estrogen receptor (ER). In some embodiments, the POI is a protein associated with neurodegeneration, e.g., a protein whose accumulation is associated with neurodegeneration. In some embodiments, the POI is a prion. In some embodiments, the POI is an amyloid protein.

In some aspects, the disclosure provides a method of identifying a test agent that destabilizes a protein of interest, the method comprising: providing cells comprising a DNA vector comprising, in operable linkage, an inducible promoter and a nucleotide sequence encoding a fusion protein comprising a protein of interest fused to a cytotoxic element; contacting a first portion of the cells with a test agent; culturing the first portion of the cells in the presence of an inducer of the inducible promoter; culturing, separately from the first portion of cells, a second portion of the cells in the presence of the inducer, wherein the second portion of the cells is not contacted with the test agent; and determining a level of cell survival in each of the cultured portions, wherein a greater level of survival in the first portion compared to the second portion indicates that the test agent destabilizes the protein of interest.

In some embodiments, the inducible promoter is a chemically inducible promoter. In some embodiments, the chemically inducible promoter is selected from the group consisting of an ethanol-inducible promoter, an IPTG-inducible promoter, a tetracycline-inducible promoter, a steroid-inducible promoter, and a metal-inducible promoter. In some embodiments, the inducer is any compound that directly or indirectly interacts with the inducible promoter to initiate or enhance transcription of the nucleotide sequence.

In some embodiments, the inducible promoter is a heat-shock inducible promoter. In some embodiments, the inducer is heat.

In some embodiments, a positive selection assay described in the application can be conducted by applying a mixture of at least 10, at least 50, at least 100, at least 1,000, at least 5,000, at least 10,000, at least 50000, at least $10^5$, at least $10^6$, at least $10^7$, at least $10^8$, at least $10^9$, or more test agents in a single vessel, culturing cells with the mixture, and determining a level of cell survival in accordance with the methods described herein. In some embodiments, if cell survival is indicative of a test agent that destabilizes a protein of interest, then a subsequent experiment can be conducted by separating test agents from the mixture to identify a particular agent responsible for cell survival. In this manner, a high throughput screen can be accomplished using any of the techniques provided in the application.

In some embodiments, a positive selection assay described in the application can be conducted by applying a single test agent at varying concentrations in different vessels, culturing cells with each concentration of the single test agent, and determining a level of cell survival in accordance with the methods described herein. In this way, dose-response can be evaluated by comparing the dose at which a test agent is able to promote cell survival in relation to a control agent that is known to promote cell survival.

In any of the foregoing embodiments, a nucleic acid encoding a fusion protein in cells further encodes a reporter protein. That is, in some embodiments, the fusion protein and the reporter protein are encoded by, or expressed from, a nucleic acid molecule having a contiguous nucleotide sequence. In some embodiments, a sequence encoding a fusion protein may be separated from a sequence encoding a reporter protein by an IRES element. Alternatively, a cleavable element can be included as described in further detail herein.

BRIEF DESCRIPTION OF DRAWINGS

The accompanying drawings are not intended to be drawn to scale. For purpose of clarity, not every component may be labeled in every drawing. In the drawings.

DETAILED DESCRIPTION

Among other aspects, the present disclosure provides new assays that use positive phenotypic characteristics of cells to identify agents that destabilize a POI. As described herein, cells expressing fusion constructs having an enzyme, which converts an exogenous substrate that is not toxic to the cells into a product that is toxic to the cells, fused to a POI may be cultured in the presence of a test agent. If the test agent destabilizes the POI (e.g., the test agent promotes degradation of, or otherwise downregulates, the POI), a corresponding decrease in the cytotoxic element fused to the POI promotes cell survival and/or cell viability. In this way, "up" assays described herein allow destabilizing agents to be identified by positive selection.

In some aspects, the present disclosure describes techniques that extend the principles disclosed in co-pending applications PCT/US2015/054893 and PCT/US2015054914, the contents of each of which are incorporated herein by reference. In this previous work, "down" assays were utilized to identify, among other things, agents that destabilize a POI. The development of down and up assays useful for identifying protein-destabilizing agents is based, at least in part, on the elucidation of a mechanism by which immunomodulatory drugs (IMiDs) may elicit cytotoxicity in cancer cells.

Figure 1:
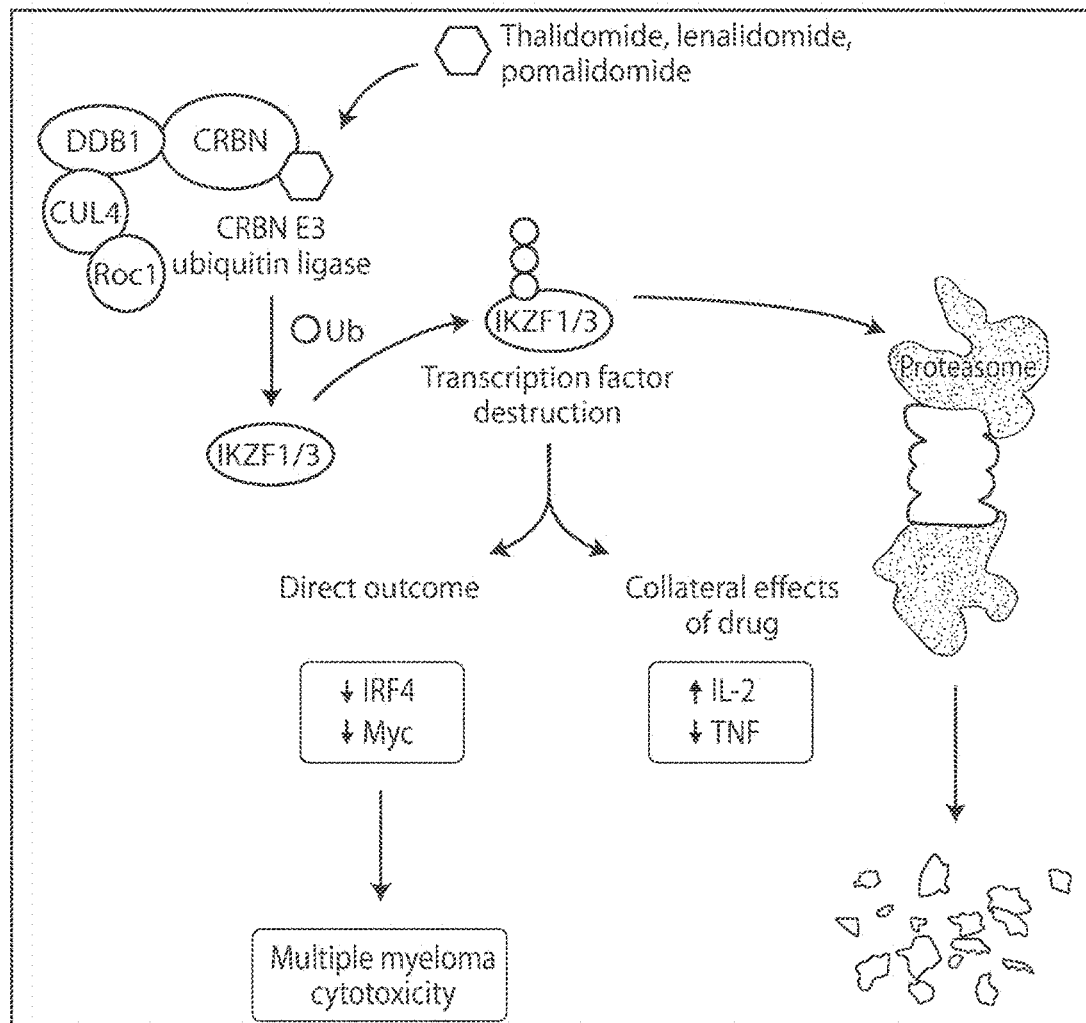
FIG. 1 is a graphical representation of a proposed mechanism by which immunomodulatory drugs (IMiDs) target IKZF proteins for degradation via ubiquitination.

Without wishing to be bound by theory, as depicted in FIG. 1, IMiDs target cereblon (CRBN), a ubiquitously expressed protein that is part of the cullin-4-containing E3 ubiquitin ligase complex CUL4-RBX1-DDB1. It is postulated that upon binding CRBN, which is the substrate recognition component of the complex, IMiDs alter the natural substrate preference of CRBN to favor binding of the oncogenic transcription factors IKZF1 and IKZF3. The subsequent ubiquitination and degradation of the transcription factors results in cancer cell cytotoxicity. Targeting cancer cells by selectively recruiting transcription factors or other critical proteins for destruction may allow for highly specified therapeutic treatments.

Accordingly, aspects of the disclosure provide methods and compositions useful for identifying agents that destabilize a POI. Such agents may be used, for example, to selectively kill a target cell that may naturally express a gene that corresponds to the POI. Conventional cell assays for agents that may elicit cytotoxic effects rely on negative selection means, such as the detection of apoptosis or an observed decrease in cell viability, to identify lead hits.

Down assays, where a hit is identified by a decrease in a detectable signal corresponding to the downregulation of the abundance or function of a POI, such as a decrease in a reporter protein signal, can be a source of artifacts, as there are typically more ways to spuriously downregulate than upregulate in biological assays. As such, the inventors have developed positive selection techniques that may be used to identify, among other things, agents that destabilize a POI. These techniques allow positive indicators, such as enhanced cell survival and increased cell viability, to be used in up assays to identify agents that destabilize a POI.

In some aspects, the techniques provided herein involve the use of cells expressing a recombinant fusion construct comprising a POI and a cytotoxic element (e.g., an enzyme or protein). In some embodiments, the cytotoxic element is a protein or an enzyme whose expression in a cell directly or indirectly promotes cytotoxicity or otherwise impairs cellular fitness. In some embodiments, the cytotoxic element is an enzyme capable of transforming an exogenous substrate that is not toxic to the cells into a product that is toxic to the cells. In some embodiments, a first portion of the cells is contacted with a test agent and cultured in the presence of the exogenous substrate. In some embodiments, a second portion of the cells, which has not been contacted with the test agent, is separately cultured in the presence of the exogenous substrate. In some embodiments, the level of cell survival is determined in each of the cultured portions. In some embodiments, a greater level of cell survival in the portion of cells contacted with the test agent compared to the portion of cells not contacted with the test agent indicates that the agent destabilizes the POI.

As used herein, a "protein of interest" (POI) may be any conceivable polypeptide or protein that may be of interest, such as to study or otherwise characterize. In some embodiments, the POI is a human polypeptide or protein. In some embodiments, the POI is an oncoprotein, such as, but not limited to, RAS, MYC, SRC, FOS, JUN, MYB, ABL, BCL2, HOX11, HOX11L2, TAL1/SCL, LMO1, LM02, ER, MYCN, MDM2, CDK4, GLI1, IGF2, EGFR, FLT3-ITD, TP53, PAX3, PAX7, BCR/ABL, HER2 NEU, FLT3R, FLT3-ITD, TAN1, B-RAF, E2A-PBX1, and NPM-ALK, as well as fusion of members of the PAX and FKHR gene families, WNT, MYC, ERK, EGFR, FGFR3, CDH5, KIT, RET, Interferon regulatory factor 4 (IRF4) and TRK. Other exemplary oncogenes are well known in the art and several such examples are described in, for example, The Genetic Basis of Human Cancer (Vogelstein, B. and Kinzler, K. W. eds. McGraw-Hill, New York, N.Y., 1998).

In some embodiments, the POI is a transcription factor. Some examples of such transcription factors include, but are not limited to, the STAT family (STATs 1, 2, 3, 4, 5a, 5b, and 6), FOS/JUN, NFκB, HIV-TAT, and the E2F family. In some embodiments, the POI is an IKAROS family zinc finger protein (IKZF). In some embodiments, the POI is IKZF1, IKZF2, IKZF3, IKZF4, or IKZF5. In some embodiments, the POI is IKZF1 or IKZF3.

In some embodiments, the POI is encoded by a nucleic acid as an open reading frame (ORF). As used herein, an "open reading frame" (ORF) refers to a sequence of nucleotides that codes for a contiguous sequence of amino acids. The translated ORF may be all or a portion of a gene encoding a protein or polypeptide of interest. In some embodiments, the ORF may be derived from an ORFeome of an organism. A complete ORFeome contains nucleic acids that encode all proteins of a given organism. In some embodiments, a representative fraction of a full ORFeome is at least 60% of all proteins expressed by the organism. In some embodiments, the organism is a mammal. In some embodiments, the mammal is human. In some embodiments, the ORF encodes a fusion protein comprising a POI fused to a cytotoxic element. As used herein, a "cytotoxic element" refers to a protein (e.g., an enzyme) whose function or activity directly or indirectly promotes cytotoxicity, or otherwise impairs cell fitness. In some embodiments, a nucleotide sequence encoding the cytotoxic element is fused to the 5' or to the 3' end of a nucleotide sequence (e.g., ORF) encoding the POI. In some embodiments, the cytotoxic element and the POI are connected via a linker. In some embodiments, the linker is a peptide linker. The peptide linker may be of any suitable length. In some embodiments, the linker does not significantly impair the function/activity of the cytotoxic element or significantly perturb the folded structure of the POI. In some embodiments, the peptide linker consists of a single amino acid. In some embodiments, the peptide consists of multiple amino acids (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, or more amino acids). In some embodiments, the linker is a unit of repeating amino acids. For example, in some embodiments, the linker contains a unit of three amino acids (e.g., Glycine-Glycine-Serine) repeated one or more times. In some embodiments, the unit of amino acids may be repeated 1, 2, 3, 4, 5, 6, 7, 8, 9, 10, 11, 12, 13, 14, 15, 16, 17, 18, 19, 20, or more times.

In some embodiments, the cytotoxic element is a protein whose function promotes cytotoxicity or otherwise impairs cell fitness. In some embodiments, the cytotoxic element is an enzyme that catalyzes the conversion of a non-cytotoxic substrate into a product that promotes cytotoxicity. In some embodiments, the product is directly cytotoxic. In some embodiments, the product undergoes further processing to elicit cytotoxicity. In some embodiments, the enzyme is deoxycytidine kinase (dCK), thymidylate kinase, thymidine kinase-guanylate kinase fusion, FKBP-Caspase9 fusion, or a derivative or variant thereof. In some embodiments, the enzyme is dCK. In some embodiments, the enzyme or protein is modified to react with an exogenous substrate. For example, the enzyme or protein may contain one or more amino acid mutations that favor reactivity with the exogenous substrate relative to an endogenous substrate of the wild-type enzyme or protein. For example, dCK can be modified as disclosed in Neschadim, A., et al. (2012) *Mol. Ther.* 20(5):1002-1013. Accordingly, in some embodiments, dCK is modified by mutating one or more amino acids at positions S74, R104, and D133. In some embodiments, dCK comprises one or more of the mutations S74E, R104M, and D133A. In some embodiments, dCK comprises the mutations S74E, R104M, and D133A. In some embodiments, dCK comprises the mutations R104M and D133A.

As used herein, an "exogenous substrate" is a substrate that is not naturally occurring in a cell expressing the POI and/or cytotoxic element. In some embodiments, the exogenous substrate is any molecule that is, by itself, non-cytotoxic, but is capable of being transformed into a product that is cytotoxic. In some embodiments, the exogenous substrate is any molecule that reacts with and/or is acted upon (directly or indirectly) by the cytotoxic element. In some embodiments, the exogenous substrate is a nucleoside analog. In some embodiments, the nucleoside analog is a modified or variant form of adenosine, guanosine, uridine, 5-methyluridine, or cytidine. In some embodiments, the nucleoside analog is a modified or variant form of deoxyadenosine, deoxyguanosine, thymidine, deoxyuridine, or deoxycytidine. In some embodiments, the exogenous substrate is a synthetic compound. In some embodiments, the synthetic compound is a nucleoside analog. In some embodiments, the nucleoside analog is bromovinyl-deoxyuridine, azidothymidine (AZT), or Ganciclovir. In some embodiments, the synthetic compound is AP1903.

In some embodiments, the exogenous substrate may be provided to the cell by any suitable method, for example, by a practitioner or by an automated process. In practice, it may be desirable to provide the exogenous substrate in an amount that is sufficient to induce a detectable increase in cytotoxicity in the absence of the test agent while also allowing for a detectable decrease in cytotoxicity in the presence of the test agent. For example, in the presence of a test agent that destabilizes a POI, the exogenous substrate should be provided to the cell in an amount that is sufficient to observe a detectable decrease in cytotoxicity when compared to a cell cultured in the absence of the test agent.

In some embodiments, the exogenous substrate is provided in a final concentration of between about 1 nM to about 100 nM, between about 100 nM to about 1 µM, between about 1 µM to about 100 µM, between about 100 µM to about 1 mM, or between about 1 mM to 100 mM. For example, the exogenous substrate is provided in a final concentration of approximately 1 nM, 10 nM, 100 nM, 1 µM, 10 µM, 100 µM, 1 mM, 10 mM, 100 mM, or more. In some embodiments, the exogenous substrate may be present in any amount that is sufficient to allow for the identification of a test agent that destabilizes a POI.

As used herein, a "test agent" may be any compound or molecule being assayed for destabilizing effects against a POI. The "destabilizing" effects refer to the downregulation and/or degradation of the POI. For example, in some embodiments, the test agent may downregulate the POI, directly or indirectly, via RNA interference. RNA interference is a process in which RNA molecules inhibit gene expression, typically by causing the destruction of mRNA molecules. Thus, in some embodiments, the test agent may destabilize the POI by degrading the mRNA encoding the POI or the mRNA of a protein that regulates POI stability. In some embodiments, the test agent may degrade the POI. For example, the test agent may elicit a selective degradation of the POI post-expression. In some embodiments, the test agent may degrade the POI via ubiquitination.

In some embodiments, test agents may include amino acids (e.g., natural amino acids, synthetic amino acids), peptides, proteins (e.g., antibodies or antigen-binding fragments thereof, artificial proteins, natural proteins), nucleosides or nucleoside analogs (e.g., cytidine, uridine, thymidine, deoxythymidine, adenosine, guanosine, and derivatives or analogs thereof), nucleotides or nucleotide analogs (e.g., nucleoside phosphates, nucleoside polyphosphates, and derivatives or analogs thereof), nucleic acids (e.g., DNA, RNA, mRNA, rRNA, tRNA, siRNA, shRNA, miRNA, sgRNA), or small organic molecules having a molecular weight of no greater than 5,000 daltons. In some embodiments, a host cell may be transformed or transfected with a plasmid or vector encoding the test agent. In some embodiments, a viral vector may be used to deliver the test agent to the host cell. In some embodiments, the viral vector is a retrovirus, lentivirus, adenovirus, adeno-associated virus, a herpes simplex virus, a baculovirus, or a derivative or pseudotype thereof. In some embodiments, the test agents are provided in a library format known in the art. For example, in some embodiments, the test agents are provided as chemically synthesized libraries, recombinantly expressed libraries (e.g., phage display libraries), or in vitro translation-based libraries (e.g., ribosome display libraries).

In some embodiments, methods and compositions described herein allow for the screening of a library of test agents to identify an agent that destabilizes a POI. In some embodiments, a library of test agents is a collection of stored agents that may be used in high-throughput screening. A library of test agents may include, for example, synthesized organic molecules, naturally occurring organic molecules, peptides, polypeptides, antibodies or antigen-binding fragments thereof, nucleic acid molecules, and components thereof. In some embodiments, the library of test agents comprises viral vectors encoding one or more test agents. In some embodiments, the library of test agents is a library of small-molecule compounds. Examples of small-molecule compound libraries include, but are not limited to, Screen-Well® Compound Libraries (Enzo Life Sciences), EXPRESS-Pick Collection and CORE Library (Chem Bridge), National Cancer Institute Library, Prestwick Chemical Library® and Tocriscreen Compound Library Collections.

In some embodiments, screening may be performed by delivering plasmid DNA encoding test agents directly to host cells. In some embodiments, screening may be performed by delivering viral vectors (e.g., viral vectors encoding a POI library, viral vectors encoding a test agent library) to the host cells. For example, in some embodiments, the library is a lentiviral plasmid library. To generate lentiviral plasmid libraries, plasmids expressing the genes being screened may be first used to make a viral library, and this viral library is subsequently used to deliver the plasmids to the host cells.

In some embodiments, screening of test agents may be performed in a pooled format. For example, in some embodiments, 10 or more test agents, 50 or more test agents, 100 or more test agents, 500 or more test agents, 1000 or more test agents, 5000 or more test agents, 10000 or more test agents, 50000 or more test agents, $10^5$ or more test agents, $10^6$ or more test agents, $10^7$ or more test agents, $10^8$ or more test agents, $10^9$ or more test agents may be screened in a pooled screening.

In some embodiments, the test agent is an IMiD. In some embodiments, an IMiD is an agent that inhibits the production of tumor necrosis factor, interleukin 6, immunoglobulin G, and/or vascular endothelial growth factor. In some embodiments, an IMiD is an agent that binds to and/or interacts (directly or indirectly) with cereblon. In some embodiments, an IMiD is any molecule that binds to and alters the substrate specificity of cereblon. In some embodiments, an IMiD is an agent that alters the natural substrate specificity of a ubiquitin ligase. In some embodiments, the test agent may be thalidomide, lenalidomide, pomalidomide, apremilast, or a derivative or analog thereof. In some embodiments, an IMiD is a small molecule. In some embodiments, an IMiD is a thalidomide-like small molecule that binds to cereblon. In some embodiments, an IMiD is a small molecule compound that binds to cereblon, altering its substrate specificity to drive ubiquitination and proteasomal destruction of Ikaros family zinc finger protein (IKZF) transcription factors.

In some embodiments, the test agent is an agent that binds to an estrogen receptor. In some embodiments, the test agent is an estrogen receptor antagonist. For example, in some embodiments, the test agent is any molecule that binds to estrogen receptors and inhibits the action of estrogen (e.g., Fulvestrant or derivatives and analogs thereof).

In some embodiments, the test agent may be provided to the cell by any suitable method, for example, by a practitioner or by an automated process. In practice, it may be desirable to provide the test agent in an amount that would be sufficient to induce a detectable decrease in cytotoxicity should the test agent destabilize a POI. For example, if the test agent is destabilizes a POI, it should be present in a cell in an amount that is sufficient to observe a detectable decrease in cytotoxicity when compared to a cell cultured in the absence of the test agent.

In some embodiments, the test agent is provided in a final concentration of between about 1 nM to about 100 nM, 100 nM to about 500 nM, between about 500 nM to about 1 µM, between about 1 µM to about 5 µM, between about 5 µM to about 10 µM, between about 10 µM to about 15 µM, between about 15 µM to about 20 µM, between about 20 µM to about 25 µM, between about 25 µM to about 30 µM, between about 30 µM to about 35 µM, between about 35 µM to about 40 µM, between about 40 µM to about 45 µM, between about 45 µM to about 50 µM, between about 50 µM to about 60 µM, between about 60 µM to about 70 µM, between about 70 µM to about 80 µM, between about 80 µM to about 90 µM, between about 90 µM to about 100 µM, between about 100 µM to about 200 µM, between about 200 µM to about 300 µM, between about 300 µM to about 400 µM, between about 400 µM to about 500 µM, between about 500 µM to about 1 mM, or more. For example, the test agent may be provided in a final concentration of approximately 1 nM, 10 nM, 100 nM, 200 nM, 300 nM, 400 nM, 500 nM, 600 nM, 700 nM, 800 nM, 900 nM, 1 µM, 2 µM, 3 µM, 4 µM, 5 µM, 6 µM, 7 µM, 8 µM, 9 µM, 10 µM, 11 µM, 12 µM, 13 µM, 14 µM, 15 µM, 16 µM, 17 µM, 18 µM, 19 µM, 20 µM, 21 µM, 22 µM, 23 µM, 24 µM, 25 µM, 26 µM, 27 µM, 28 µM, 29 µM, 30 µM, or more. In some embodiments, the test agent may be present in any amount that is sufficient to allow for a detectable change in cytotoxicity should the test agent destabilize a POI.

As used herein, "cytotoxic," "cytotoxicity," and "toxic to a cell" are used interchangeably, and refer to the ability to kill a cell or otherwise impair cellular fitness. In some embodiments, cytotoxicity may result in a decrease in cell growth and/or cell proliferation in vitro or in vivo. In some embodiments, cytotoxicity and/or the level of cell survival may be evaluated as a decrease in cell viability. In some embodiments, cytotoxicity and/or the level of cell survival may be evaluated by other characteristics of cell growth, such as anchorage independence, semi-solid or soft agar growth, changes in contact inhibition and density limitation of growth, changes in growth factor or serum requirements, changes in cell morphology, gaining or losing immortalization, or changes in specific markers.

In some embodiments, assays described herein evaluate cytotoxicity and/or cell survival to identify agents that may destabilize a POI. In some embodiments, cytotoxicity and/or the level of cell survival may be evaluated by measuring cell viability or cell number, either directly or indirectly. Many such methods of measuring cell viability or cell number are known in the art and commercially available. These include methods that generate signals via fluorescence, calorimetrically, by radioactivity, or other common signaling systems. In some embodiments, cell survival and/or cytotoxicity may be evaluated based on reporter proteins (e.g., fluorescent reporter proteins). In some embodiments, cytotoxicity and/or the level of cell survival may be evaluated by flow cytometry. In some embodiments, cytotoxicity and/or the level of cell survival may be evaluated by fluorescence-activated cell sorting (FACS).

In some embodiments, cell viability may be assessed by measuring one or more different endpoints including, but not limited to, levels of cytoplasmic enzymes, permeability of cells to dyes, DNA fragmentation, release of a radioisotopic label such as $^{51}Cr$, or other formats. In some embodiments, cell viability is measured using an assay suitable for a high throughput screening format, such as a colorimetric or fluorescent viability assay. For example, an Alamar blue (AB) assay incorporates a redox indicator that changes the color or fluorescence in response to metabolic activity. The Alamar blue fluoresces in the presence of living, but not dead, cells. Such an assay can be conveniently read in a microplate or by flow cytometry. Colorimetric assays such as the MTT assay, which measures the reduction of MTT (3-(4.5-dimethyl) thiazol-2-yl-2,5-diphenyl tetrazolium bromide) to formazan, may also be used conveniently in a high throughput format to measure cell viability and proliferation.

In some embodiments, assays that measure cell number may be used to determine the level of cell survival. In some embodiments, cell number may be evaluated by measuring the intercalation of dyes into the DNA of a cell, where the amount of intercalated dye is directly proportional to cell number. For example, cells can be stained with a dye such as Hoechst 33342, which intercalates in the DNA of vital cells, and cell number is determined by measuring the amount of fluorescence. In some embodiments, cells may be directly counted.

The compositions and methods described herein may utilize any suitable host cell type. In some embodiments, the host cell is a bacterial cell, a yeast cell, an insect cell, an amphibian cell, a plant cell, or a mammalian cell. Suitable host cells include, but are not limited to, bacterial cells (e.g., *E. coli, Bacillus subtilis*, and *Salmonella typhimurium*), yeast cells (e.g., *Saccharomyces cerevisiae* and *Schizosaccharomyces pombe*), plant cells (e.g., *Nicotiana tabacum* and *Gossypium hirsutum*), and mammalian cells (e.g., CHO cells, and 3T3 fibroblasts, HEK 293 cells, U-2 OS cells). In some embodiments, the host cell is a HEK293 cell. In some embodiments, the host cell is a HEK293FT cell.

In some aspects, positive selection assays described herein may involve contacting the host cell with one or more exogenously provided molecules. For example, in some embodiments, a host cell having an expression construct described herein (e.g., expressing a POI, a cytotoxic element and/or a POI-cytotoxic element fusion) may be contacted with an exogenous substrate and/or a test agent. In some embodiments, the exogenous substrate is contacted with the host cell having the expression construct before the test agent is contacted with the host cell. In some embodiments, the exogenous substrate is contacted with the host cell having the expression construct after the test agent is contacted with the host cell. In some embodiments, the exogenous substrate and the test agent are contacted with the host cell having the expression construct at approximately the same time. In some embodiments, the exogenous substrate and/or the test agent may be contacted with a host cell prior to the host cell being transfected/transformed with the expression construct.

In some embodiments, contacting the host cells having an expression construct described herein with an exogenous substrate and/or test agent comprises growing the host cells in the presence of the exogenous substrate and/or test agent for an appropriate time under suitable culture conditions. Suitable culture conditions, including the duration of the culture, will vary depending on the cell being cultured. However, one skilled in the art can easily determine the culture conditions by following standard protocols, such as those described in the series Methods in Microbiology, Academic Press Inc. Typically, the cell culture medium (e.g., DMEM) may contain any of the following nutrients in appropriate amounts and combinations: salt(s), buffer(s), amino acids, glucose or other sugar(s), antibiotics (e.g., penicillin, blasticidin, ampicillin, spectinomycin, streptomycin, kanamycin, chloramphenicol, etc.), serum or serum replacement (e.g., FBS, BSA), and other components such as, but not limited to, peptide growth factors, cofactors, and trace elements. In some embodiments, the host cells are grown in the presence of the exogenous substrate and/or the test agent for 15 minutes, 30 minutes, 1 hour, 2 hours, 4 hours, 6 hours, 8 hours, 10 hours, 12 hours, 14 hours, 16 hours, 18 hours, 20 hours, 24 hours, 30 hours, 48 hours, 72 hours, or 96 hours.

In some embodiments, constructs described herein may be introduced to a host cell by any suitable method. In some embodiments, a host cell may be transformed or transfected with a plasmid encoding the construct. In some embodiments, a viral vector may be used to deliver the construct to the host cell. In some embodiments, the viral vector is a retrovirus, lentivirus, adenovirus, adeno-associated virus, a herpes simplex virus, a baculovirus, or a derivative or pseudotype thereof.

In some embodiments, constructs described herein comprise nucleic acids encoding one or more elements in operable linkage. As used herein, "operable linkage" refers to a functional linkage between two nucleic acid sequences, such as a transcription control element (e.g., a promoter) and the linked transcribed sequence. Thus, a promoter is in operable linkage with a gene if it can mediate transcription of the gene.

As used herein, a "promoter" usually contains specific DNA sequences (responsive elements) that provide binding sites for RNA polymerase and transcriptional factors for transcription to take place. In some embodiments, the promoter is a eukaryotic promoter or a synthetic promoter. Examples of promoters include, but are not limited to, the TATA box, the SV40 late promoter from simian virus 40, cytomegalovirus (CMV) promoter, ubiquitin C promoter (UbC promoter) and the T7 promoter. These and other promoter sequences are well known in the art. In some embodiments, the promoter is a CMV promoter. In some embodiments, the promoter is a UbC promoter. In some embodiments, the promoter is an inducible promoter.

As used herein, an "inducible promoter" refers to a transcriptional control element that can be regulated in response to specific signals. In some embodiments, an inducible promoter is transcriptionally active when bound to a transcriptional activator, which in turn is activated under a specific set of conditions, for example, in the presence of a particular combination of chemical signals that affect binding of the transcriptional activator to the inducible promoter and/or affect function of the transcriptional activator itself. Thus, an inducible promoter is a promoter that, either in the absence of an inducer, does not direct expression, or directs low levels of expression, of a nucleic acid sequence to which the inducible promoter is operably linked; or exhibits a low level of expression in the presence of a regulating factor that, when removed, allows high-level expression from the promoter (e.g., a tetracycline-inducible promoter). In the presence of an inducer, an inducible promoter directs transcription at an increased level.

Inducible promoters can be divided into two categories according to their induction conditions: those inducible by abiotic factors (e.g., temperature, light, chemical substances) and those that can be induced by biotic factors (e.g., pathogen or pest attack). Examples of the first category include, but are not limited, heat-inducible (US 05187287) and cold-inducible (US05847102) promoters, copper-inducible promoters (Mett et al., 1993, Proc. Natl. Acad. Sci., 9O1 4567-4571), steroid-inducible promoters (Aoyama & Chua, 1997, Plant J., H, 605-612; McNellis et al., 1998, Plant J., T4, 247-257; US06063985), ethanol-inducible promoters (Caddick et al., 1997, Nature Biotech., 16, 177-180; WO09321334; WO0109357; WO02064802), isopropyl beta-D-thiogalactopyranoside (IPTG)-inducible promoters (Wilde et al., 1992, EMBO J., 11:1251-1259), and tetracycline-inducible promoters (Weinmann et al., 1994, Plant J., 5, 559-569). For a review on chemically inducible systems see: Zuo & Chua, (2000, Current Opin. Biotechnol., H1 146-151) and Moore et al., (2006, Plant J., 45: 651-683). Other constitutive, inducible, and cell type-specific regulatory elements are well known in the art.

As used herein, an "internal ribosomal entry site" or "IRES" is a cis acting nucleic acid element that mediates the internal entry of ribosomes on an RNA molecule and thereby regulates translation in eukaryotic systems. In the methods and compositions of the present disclosure, one or more IRES elements may be contained in the plasmid. The one or more IRES elements permit the independent translation of a nucleotide sequence encoding, for example, one or more reporter proteins, an ORF, or an ORF fused to a nucleotide sequence encoding a cytotoxic element from a single messenger RNA. In some embodiments, the one or more IRES elements are the same (i.e., they have identical sequences). In some embodiments, the one or more IRES elements are not the same (i.e., they do not have identical sequences).

Many IRES elements have been identified in both viral and eukaryotic genomes. In addition, synthetic IRES elements have also been developed. For example, IRES elements have been found in a variety of viruses including members of the genus Enterovirus (e.g. human poliovirus 1 (Ishii et al. (1998) J Virol. 72:2398-405 and Shiroki et al. (1997) J. Virol. 77:1-8), human Coxsackievirus B); Rhinovirus (e.g., human rhinovirus); Hepatovirus (Hepatitis A virus); Cardiovirus (Encephalomyocarditis virus ECMV (nucleotides 2137-2752 of GenBank Accession No. AB041927 and Kim et al. (1992) Mol Cell Biology 72:3636-43) and Etheirler's encephalomyelitis virus); Aphtovirus (Foot- and mouth disease virus (nucleotides 600-1058 of GenBank Accession No. AF308157; Belsham et al. (1990) EMBO 77:1105-10; Poyry et al. (2001) RNA 7:647-60; and Stoneley et al. (2000) Nucleic Acid Research 25:687-94), equine rhinitis A virus, Ewuine rhinitis B); Pestivirus (e.g., Bovine viral diarrhea virus (Poole et al. (1995) Virology 206:150-154) and Classical swine fever virus (Rijnbrand et al. (1997) J. Virol 77:451-7); Hepacivirus (e.g., Hepatitis C virus (Tsukiyama-Kohara et al. (1992) J. Virol. 66:1476-1483, Lemon et al. (1997) Semin. Virol. 5:274-288, and nucleotide 1201-1812 of GenBank Accession No. AJ242654.) and GB virus B). Each of these references is herein incorporated by reference.

IRES elements have also been found in viruses from the family Retroviridae, including members of the Lentivirus family (e.g., Simian immunodeficiency virus (Ohlmann et al. (2000) Journal of Biological Chemistry 275:11899-906)

and human immunodeficiency virus 1 (Buck et s/. (2001) J Virol. 75:181-91); the BLV-HTLV retroviruses (e.g., Human T-lymphotrophic virus type 1 (Attal et al. (1996) EEES Letters 392:220-4); and the Mammalian type C retoviral family (e.g., Moloney murine leukemia virus (Vagner et al. (1995) J. Biol. Chem 270:20316-83), Friend murine leukemia virus, Harvey murine sarcoma virus, Avian retriculoendotheliosis virus (Lopez-Lastra et al. (1997) Hum. Gene Ther 5:1855-65), Murine leukemia virus (env RNA) (Deffaud et al. (2000) J. Virol. 74:846-50), Rous sarcoma virus (Deffaud et al. (2000) J. Virol. 74:11581-8). Each of these references is herein incorporated by reference.

Some eukaryotic mRNAs also contain IRES elements including, for example, BiP (Macejak et al. (1991) Nature 355:91); Antennapedia of Drosophilia (exons d and e) (Oh et al. (1992) Genes and Development 6:1643-1653; c-myc; and, the X-linked inhibitor of apoptosis (XIAP) gene (U.S. Pat. No. 6,171,821).

Various synthetic IRES elements have been generated. See, for example, De Gregorio et al. (1999) EMBO J. 75:4865-74; Owens et al. (2001) PNAS 4:1471-6; and Venkatesan et al. (2001) Molecular and Cellular Biology 21:2826-37. For additional IRES elements known in the art, see, for example, rangueil.inserm.fr/IRESdatabase.

In some embodiments, an IRES element is not included in nucleic acid constructs of the present disclosure. Alternative methods are known in the art that provide for the ability to introduce distinct recombinant elements into a cell from the same nucleic acid. For example, in some embodiments, a cleavable element may be inserted in place of an IRES element. In some embodiments, a cleavable element may comprise a naturally cleavable site. The transcribed or translated product comprising the site would be cleaved by cellular machinery to generate two distinct products. Such naturally cleavable sites are known in the art. For example, the P2A peptide sequence derived from is a self-cleaving peptide linker from a porcine teschovirus that can substitute for an IRES. There are other sequences from other viruses that are self-cleaving, e.g., T2A sequences.

In some aspects, the techniques provided herein involve the use of a mixture of cells comprising a first portion of cells and a second portion of cells. In some embodiments, the first portion of cells expresses a recombinant fusion protein comprising a POI and a cytotoxic element (e.g., an enzyme or protein). In some embodiments, the cytotoxic element is an enzyme capable of transforming an exogenous substrate that is not toxic to the cells into a product that is toxic to the cells. In some embodiments, the second portion of cells expresses a recombinant protein comprising the enzyme (e.g., the enzyme not fused to the POI). In some embodiments, the mixture of cells is contacted with a test agent. In some embodiments, the mixture of cells is cultured in the presence of the exogenous substrate. In some embodiments, the level of cell survival is determined for each of the portions in the cultured mixture. In some embodiments, a ratio of the number of cells in the first portion to the number of cells in the second portion in the mixture greater than 1 indicates that the test agent destabilizes the POI.

As used herein, a "cell mixture" refers to a single sample of cells having at least a first portion of cells transformed or transfected with a first expression vector and a second portion of cells transformed or transfected with a second expression vector, where the first and second expression vectors are different. In some embodiments, the cells of each portion of cells in the mixture are of the same type. In some embodiments, the cells of each portion of cells in the mixture are not of the same type. In some embodiments, it may be advantageous to utilize cells that are capable of being identified as corresponding to a particular portion of cells in the mixture. For example, in some embodiments, each portion of cells has a unique detectable element that allows for the determination of the relative presence of each portion in the cell mixture. In some embodiments, the detectable element is a reporter protein.

As used herein, a "reporter protein" is any protein that can be specifically detected when expressed (i.e., has a detectable signal when expressed), for example, via its fluorescence or enzyme activity. In some embodiments, the first portion of cells (e.g., expressing the recombinant fusion protein) in the cell mixtures described herein further expresses a first reporter protein. In some embodiments, the second portion of cells (e.g., expressing the cytotoxic element) in the cell mixtures described herein further expresses a second reporter protein. In some embodiments, the first reporter protein and/or the second reporter protein is encoded by the same construct(s) encoding the recombinant proteins.

Typically, the first and second reporter proteins have distinguishable detectable reporter signals. For example, the first and second reporter proteins are enzyme proteins having distinguishable signals generated from their products. In some embodiments, the first and second reporter proteins are bioluminescent proteins that emit light at different wavelengths and/or utilize different substrates. Alternatively, the first and second reporter proteins are fluorescent proteins that fluoresce at different wavelengths.

Many reporter proteins known in the art may be used, including but not limited to bioluminescent proteins, fluorescent reporter proteins, and enzyme proteins such as beta-galactosidase, horseradish peroxidase and alkaline phosphatase that produce specific detectable products. The fluorescent reporter proteins include, for example, green fluorescent protein (GFP), cyan fluorescent protein (CFP), red fluorescent protein (RFP), and yellow fluorescent protein (YFP), as well as modified forms thereof, e.g., enhanced GFP (EGFP), enhanced CFP (ECFP), enhanced RFP (ERFP), mCHERRY, and enhanced YEP (EYEP).

Examples of bioluminescent proteins, such as luciferases, including but not limited to renilla luciferase (Rluc), firefly luciferase (FLuc), and NanoLuc, are known in the art (see, for example, Fan, F. and Wood, K., Assay and drug development technologies V5 #1 (2007); Gupta, R. et al Nature Methods V8 #10 (2011); Nano-Glo® Luciferase Assay System (Promega) and en.wikipedia.org/wiki/Bioluminescence.

Other non-limiting examples of reporter proteins are shown below:

| Species-specific luciferase specificity, cofactor requirements and physical characteristics. | | | | | |
|---|---|---|---|---|---|
| Organism | Luciferase | Size (kDa) | Substrate | Requires | Secreted |
| *Photinus pyralis* | North American firefly luciferase | 61 | D-luciferin | Mg, ATP | No |

Species-specific luciferase specificity, cofactor requirements and physical characteristics.

| Organism | Luciferase | Size (kDa) | Substrate | Requires | Secreted |
|---|---|---|---|---|---|
| *Luciola cruciata* | Japanese firefly (Genji-botaru) luciferase | 64 | D-luciferin | Mg, ATP | No |
| *Luciola italica* | Italian firefly Luciferase | 64 | D-luciferin | Mg, ATP | No |
| *Luciola lateralis* | Japanese firefly (Heike) luciferase | 64 | D-luciferin | Mg, ATP | No |
| *Luciola mingrelica* | East European firefly luciferase | 64 | D-luciferin | Mg, ATP | No |
| *Photuris pennsylvanica* | Pennsylvania firefly luciferase | 64 | D-luciferin | Mg, ATP | No |
| *Pyrophorus plagiophthalamus* | Click beetle luciferase | 64 | D-luciferin | Mg, ATP | No |
| *Phrixothrix hirtus* | Railroad worm luciferase | 64 | D-luciferin | Mg, ATP | No |
| *Renilla reniformis* | *Renilla* luciferase | 36 | Coelenterazine | N/A | No |
|  | Rluc8 (mutant of *Renilla* luciferase) | 36 | Coelenterazine | N/A | No |
|  | Green *Renilla*, luciferase | 36 | Coelenterazine | N/A | No |
| *Gaussia princeps* | *Gaussia* luciferase | 20 | Coelenterazine | N/A | Yes |
|  | *Gaussia*-Dura luciferase | 20 | Coelenterazine | N/A | Yes |
| *Cypridina noctiluca* | Cypridine luciferase | 62 | Vargulin/Cypridina luciferin | N/A | Yes |
| *Cypridina hilgendorfii* | *Cypridina* (Vargula) luciferase | 62 | Vargulin/Cypridina luciferin | N/A | Yes |
| *Metridia longa* | *Metridia* luciferase | 23.8 | Coelenterazine | N/A | Yes |
| *Oplophorus gracilorostris* | OLuc | 19 | Coelenterazine | N/A | Yes |

In some embodiments, the first and second reporter proteins are selected from the group consisting of renilla luciferase (Rluc), firefly luciferase (FLuc), and NanoLuc. In some embodiments, the first and second reporter proteins are selected from the group consisting of green fluorescence protein and tdTomato. In some embodiments, the first and second reporter proteins are selected from the group consisting of TagBFP, mTagBFP2, Azurite, EBFP2, mKalamal, Sirius, SBFP2, Sapphire, T-Sapphire, Aquamarine, ECFP, Cerulean, mCerulean3, CyPet, mCFPm, SCFP3A, mTurquoise, mTurquoise2, AmCyanl, MiCy (Midoriishi-Cyan), TagCFP, mTFP1, iLOV, AcGFP1, EGFP, Emerald, Superfolder GFP, monomeric Azami Green, cfSGFP2, ZsGreen, TagGFP2, mUKG, mWasabi, Clover, mClover2, mNeonGreen, EYFP, Topaz, mCitrine, Venus, YPet, ZsYellowl, mPapayal, SYFP2, TagYFP, monomeric Kusabira-Orange, mKOK, mKO2, mOrange, mOrange2, TurboRFP, mRaspberry, J-red, DsRed-monomer, mCherry, mStrawberry, mTangerine, TagRFP, TagRFP-T, mApple, mRuby, mRuby2, eqFP611, DsRed2, FusionRed, mPlum, mCrimson3, dKatushka, HcRed-Tandem, mKatel.3, mCardinal, mKate2, mNeptune, NirFP, TagRFP657, IFP1.4, iRFP, mKeima Red, LSS-mKatel, LSS-mKate2, mBeRFP, PA-GFP, PAmCherry1, PATagRFP, Kaede (green), Kaede (red), KikGR1 (green), KikGR1 (red), PS-CFP2, mEos2 (green), mEos2 (red), PSmOrange, and Dronpa. In some embodiments, the reporter proteins can be used to determine the relative presence of each portion of cells at any point (e.g., prior to culturing, during culturing, or after culturing).

In some embodiments, it may be preferable to provide a mixture of cells having a known ratio of cell portions prior to culturing. In this way, a ratio obtained after culturing can be compared to evaluate the effects of culturing under a particular condition. For example, in some embodiments, the ratio of the first portion (e.g., expressing the POI fusion) to the second portion (e.g., expressing the cytotoxic element) in the mixture is less than 1 prior to culturing. As destabilization of the POI increases the level of cell survival, having an initially lower relative amount of the first portion provides a wider spectrum by which growth rescue by the test agent can be assessed. In some embodiments, the ratio of the first portion to the second portion prior to culturing is between about 0.0001 and 0.0005, between about 0.0005 and 0.001, between about 0.001 and 0.005, between about 0.005 and 0.01, between about 0.01 and 0.05, between about 0.05 and 0.1, between about 0.1 and 0.2, between about 0.2 and 0.3, between about 0.3 and 0.4, between about 0.4 and 0.5, between about 0.5 and 0.6, between about 0.6 and 0.7, between about 0.7 and 0.8, between about 0.8 and 0.9, or between about 0.9 and 0.99. In some embodiments, the ratio of the first portion to the second portion prior to culturing is approximately 0.1, 0.01, or 0.001. In some embodiments, the ratio of the first portion to the second portion prior to culturing is compared to the ratio during and/or after culturing.

In some embodiments, the ratio of the number of cells in the first portion to the number of cells in the second portion in the mixture after culturing may be used to evaluate whether a test agent destabilizes the POI. In some embodiments, a ratio of the number of cells in the first portion to the number of cells in the second portion in the cultured mixture that is greater than 1 indicates that the test agent destabilizes the POI. A ratio that is greater than 1 indicates that the portion of cells expressing the POI fusion construct are present in the cell mixture to a greater extent than any other portion of cells, and is therefore indicative of destabilization of the POI. In some embodiments, the ratio of the first portion to the second portion after culturing is between about 1.0 and 2.0, between about 2.0 and 3.0, between about 3.0 and 4.0, between about 4.0 and 5.0, between about 5.0 and 6.0, between about 7.0 and 8.0, between about 8.0 and 9.0, between about 9.0 and 10.0, between about 10.0 and 20.0, between about 20.0 and 30.0, between about 30.0 and 40.0, between about 40.0 and 50.0, between about 50.0 and 60.0, between about 60.0 and 70.0, between about 70.0 and 80.0, between about 80.0 and 90.0, or between about 90.0 and 99.9.

In some embodiments, a fusion construct comprising a POI fused to a cytotoxic element may be inherently less stable than a construct comprising the cytotoxic element (e.g., an unfused cytotoxic element). Accordingly, in methods relating to the use of cell mixtures, this inherent instability could result in slight enrichment of cells expressing the fusion construct in the absence of any destabilizing agent. Thus, in some embodiments, it may be desirable to compare a cell mixture cultured in the presence of a test agent to a cell mixture cultured in the absence of the test agent to determine whether the test agent destabilizes the protein of interest. A ratio of the number of cells in the first portion to the number of cells in the second portion in the mixture of cells can be determined for each condition, as described herein. In such embodiments, a destabilizing agent may be identified when the ratio for the mixture contacted with the test agent exceeds the ratio for the mixture not contacted with the test agent. In some aspects, the up assays described herein may be advantageously performed in an arrayed, or multiwell, format (e.g., high-throughput screening). In some embodiments, it may be desirable to screen a large number of test agents (e.g., 10 or more, 50 or more, 100 or more, 500 or more, 1000 or more, 5000 or more, 10000 or more, 50000 or more, 100000 or more test agents). In some embodiments, screening large numbers of test agents may require parallel handling and processing of many test agents and assay component reagents. Using robotics, data processing and control software, liquid handling devices, and sensitive detectors, High-throughput screening allows a researcher to quickly conduct millions of chemical, genetic, or pharmacological tests. Through this process, one can rapidly identify active molecules, compounds, antibodies, or genes that modulate a particular biomolecular pathway. The results of these experiments provide starting points for drug design and for understanding the interaction or role of a particular biochemical process in biology. An important component of high-throughput screening is the use of a microtiter plate, which is a small container that features a grid of sample wells.

In some embodiments, assays described herein may be conducted in sample wells of a microtiter plate. In some embodiments, the microtiter plate may have 96, 384, 1536, or 3456 sample wells. In some embodiments, the number of sample wells on a microtiter plate is a multiple of 96. In some embodiments, each sample well may contain some or all reagents necessary to perform the assays described herein. In some embodiments, each sample well may contain all reagents except for a test agent. In some embodiments, the test agent may be the last reagent added to the sample well.

At any point during the high-throughput screen, sample wells may be monitored to evaluate the progress of the assay. In some embodiments, sample wells are monitored manually or by an automated process. In some embodiments, sample wells are monitored by microscopy to assess changes or defects in cells. In some embodiments, sample wells are monitored by measuring absorption, fluorescence emission, optical density, or radioactivity. In some embodiments, automated monitoring of a sample well integrates the signal from all the material in the well, giving an overall population average of all the molecules in the well. In some embodiments, this information can be used to identify lead compounds/agents.

EXAMPLES

Example 1

Cell Culture

HEK-293FT (Invitrogen) cells were maintained in DMEM medium supplemented with 10% FBS, 100 U/mL Penicillin and 100 µg/mL streptomycin. Stable cell lines were established by lentiviral infection followed by growth in media containing 10 µg/mL blasticidin, followed by fluorescence activated cell sorting to collect GFP-expressing cells.

Plasmids

The destination vectors pCMV-Gateway-V5-IRES-GFP and pCMV-Gateway-IRES-Tomato were generated by cloning the respective IRES-GFP and IRES-Tomato sequences from pLeGO-IG2 and pLeGO-IT2 vectors (ClonTech) into the NheI/AgeI sites of pLX304. The EV (empty vector), dCK (deoxycytidine kinase) IKZF3 (Aiolos) and IKZF3 (Q147H) as well as dCK-IKZF3, dCK-IKZF34 (Q147H), IKZF3-dCK and IKZF3 (Q147H)-dCK fusions generated by overlapping PCR were cloned into pDONR223 by BP recombination, and subsequently cloned into pCMV-Gateway-V5-IRES-GFP and pCMV-Gateway-IRES-Tomato by LR recombination, and the resulting clones were analyzed by fluorescence activated cell sorting to collect GFP or Tomato-expressing cells respectively.

The destination vector pCMV-dCK-Gateway-V5-IRES-GFP and pCMV-Gateway-dCK-V5-IRES-GFP were generated using the InFusion HD Cloning Kit (ClonTech) to recombine the dCK sequence into pCMV-Gateway-V5-IRES-GFP as in in-frame fusion immediately 5' or 3' to the Gateway sequence.

The destination vectors pCMV-ThomaDegron-Gateway-V5-IRES-GFP and pCMV-Gateway-ThomaDegron-V5-IRES-GFP were generated using the Infusion Cloning HD Kit (ClonTech) to encode IKZF3 residues 73-200 as an in-frame fusion either immediately 5' or 3' to the Gateway sequence, respectively.

The Estrogen Receptor (ER) was cloned into the pDONR223 vector by BP cloning, and then shuttled into the pCMV-Gateway-V5-IRES-GFP destination vector by LR cloning to generate pCMV-ER-V5-IRES-GFP, as well as into the pCMV-dCK-Gateway-V5-IRES-GFP and pCMV-Gateway-dCK-V5-IRES-GFP to generate the expression clones pCMV-dCK-ER-V5-IRES-GFP and pCMV-ER-dCK-V5-1RES-GFP respectively.

Example 2

Positive Selection of IKZF Protein Destabilizers

Cereblon is a protein component of an ubiquitin ligase complex and is responsible for substrate recognition. As part of the complex, cereblon binds an endogenous substrate while a separate component of the complex ubiquitinates the substrate, thereby tagging it for degradation. Immunomodulatory drugs (IMiDs) are small molecule compounds that bind to cereblon, altering its substrate specificity to drive ubiquitination and proteasomal destruction of Ikaros family zinc finger protein (IKZF) transcription factors (FIG. 1). The selectively degraded IKZF proteins (namely, IKZF1 and IKZF3) are essential transcription factors in myeloma cells. When exposed to IMiD compounds, IKZF1/3 levels are diminished in myeloma cells and the result is cytotoxicity.

Figure 2:
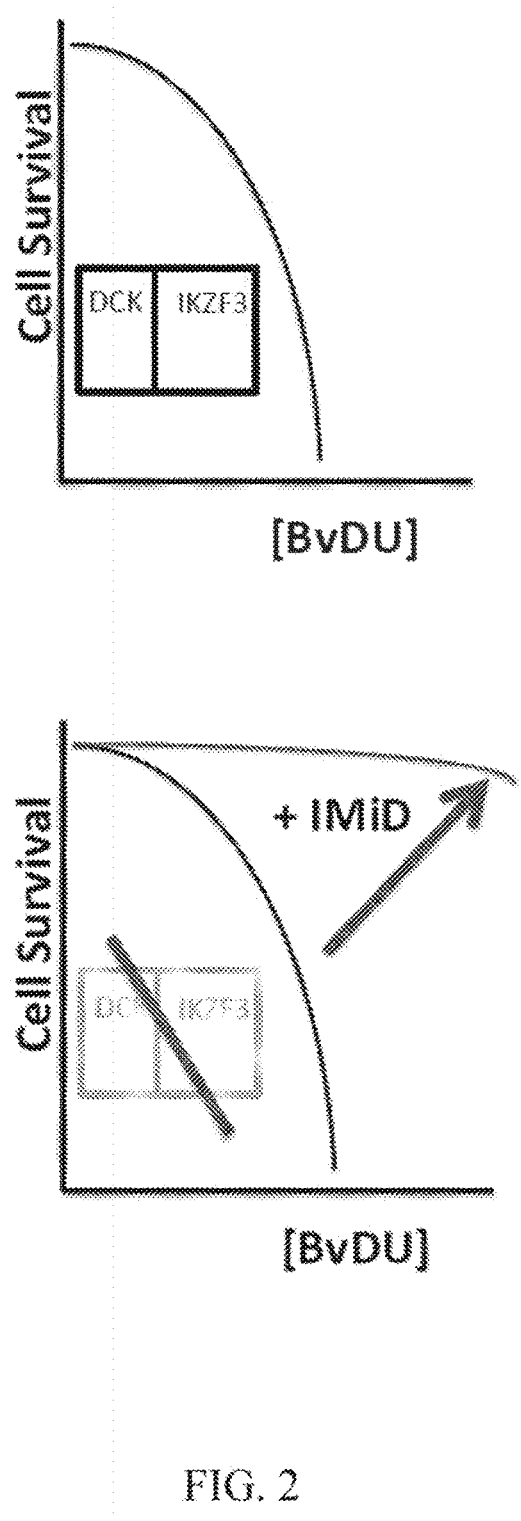
FIG. 2 illustrates positive selection of IKZF3 destabilizing agents, in accordance with some embodiments of the compositions and methods described herein.

To select for novel molecules having function analogous to IMiD compounds, a positive selection system was developed that, for proof of concept purposes, utilizes a fusion construct having a target protein (IKZF3) and an enzyme whose activity elicits a cytotoxic response. Deoxycytidine kinase (dCK) can phosphorylate synthetic nucleoside analogs, such as bromovinyl-deoxyuridine (BVdU), which results in toxicity and cell death. The synthetic nucleoside analog substrate is not normally cytotoxic. However, once phosphorylated by dCK, the nucleoside analog product can undergo further endogenous processing to elicit various cytotoxic effects. Thus, expression of a dCK-IKZF3 fusion construct in the presence of increasing concentrations of BVdU would produce a concomitant decrease in cell survival (FIG. 2, top). The addition of a molecule with IMiD-like properties would presumably tag the fusion construct having IKZF3 for degradation, ultimately rescuing the cell from cytotoxicity that would otherwise result from phosphorylated BVdU (FIG. 2, bottom).

Figure 3:
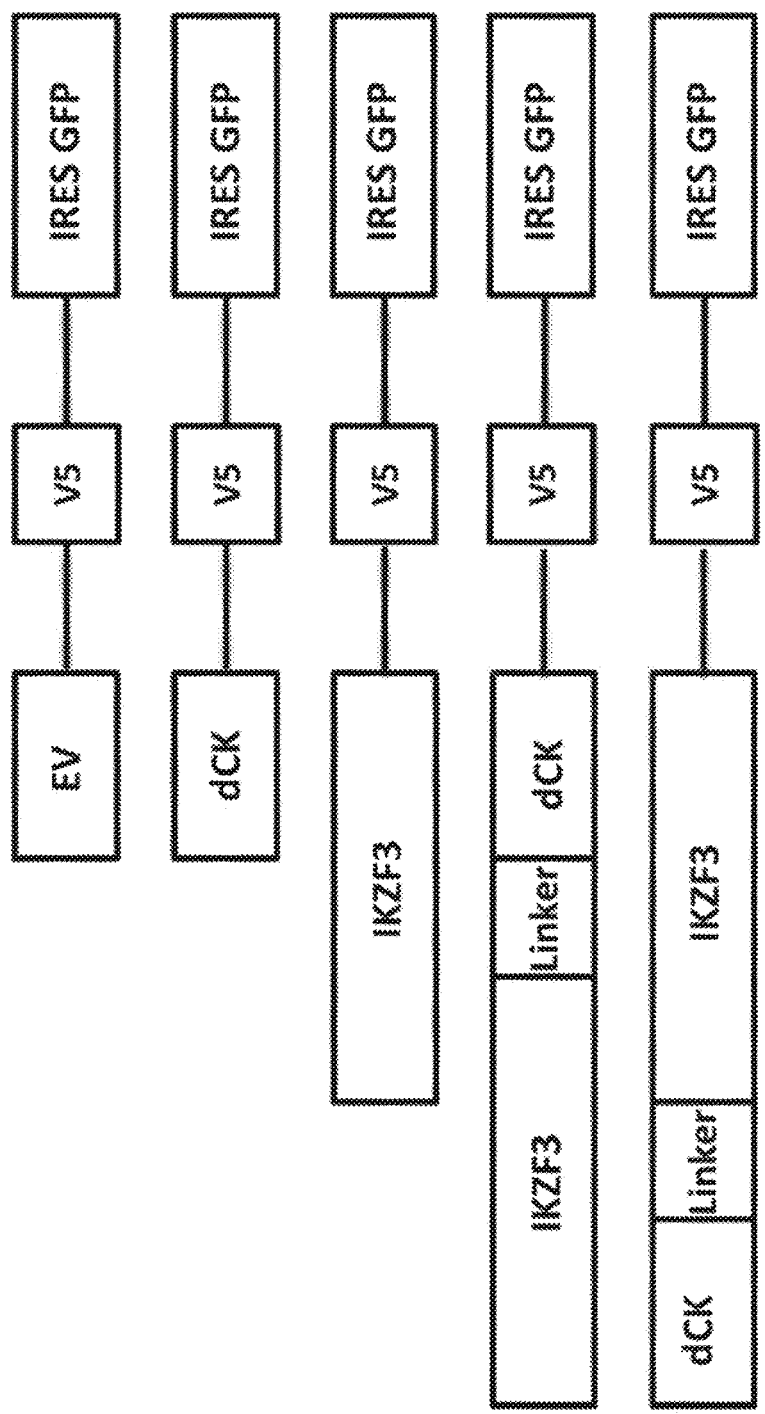
FIG. 3 shows non-limiting constructs useful for positive selection of IKZF3 destabilizing agents, in accordance with some embodiments of the compositions and methods described herein.
Figure 4:
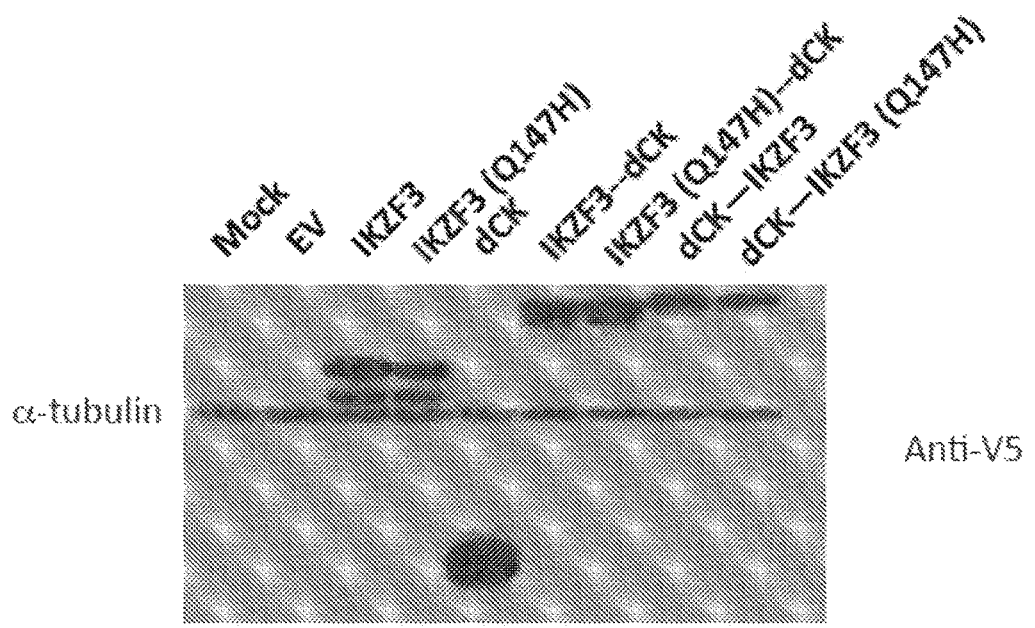
FIG. 4 depicts protein expression, via SDS-PAGE, of control and IKZF3 fusion constructs utilized in certain embodiments of the techniques described herein.

Lentiviral expression vectors were designed as depicted in FIG. 3, and selected constructs were obtained by the cloning procedures described above. For these experiments, a [Gly-Gly-Ser]$_8$ linker was used in the fusion constructs to connect dCK enzyme to IKZF3 protein. SDS-PAGE and anti-V5 rabbit polyclonal antibody probes verified expression of the constructs, as shown in FIG. 4.

Figure 5:
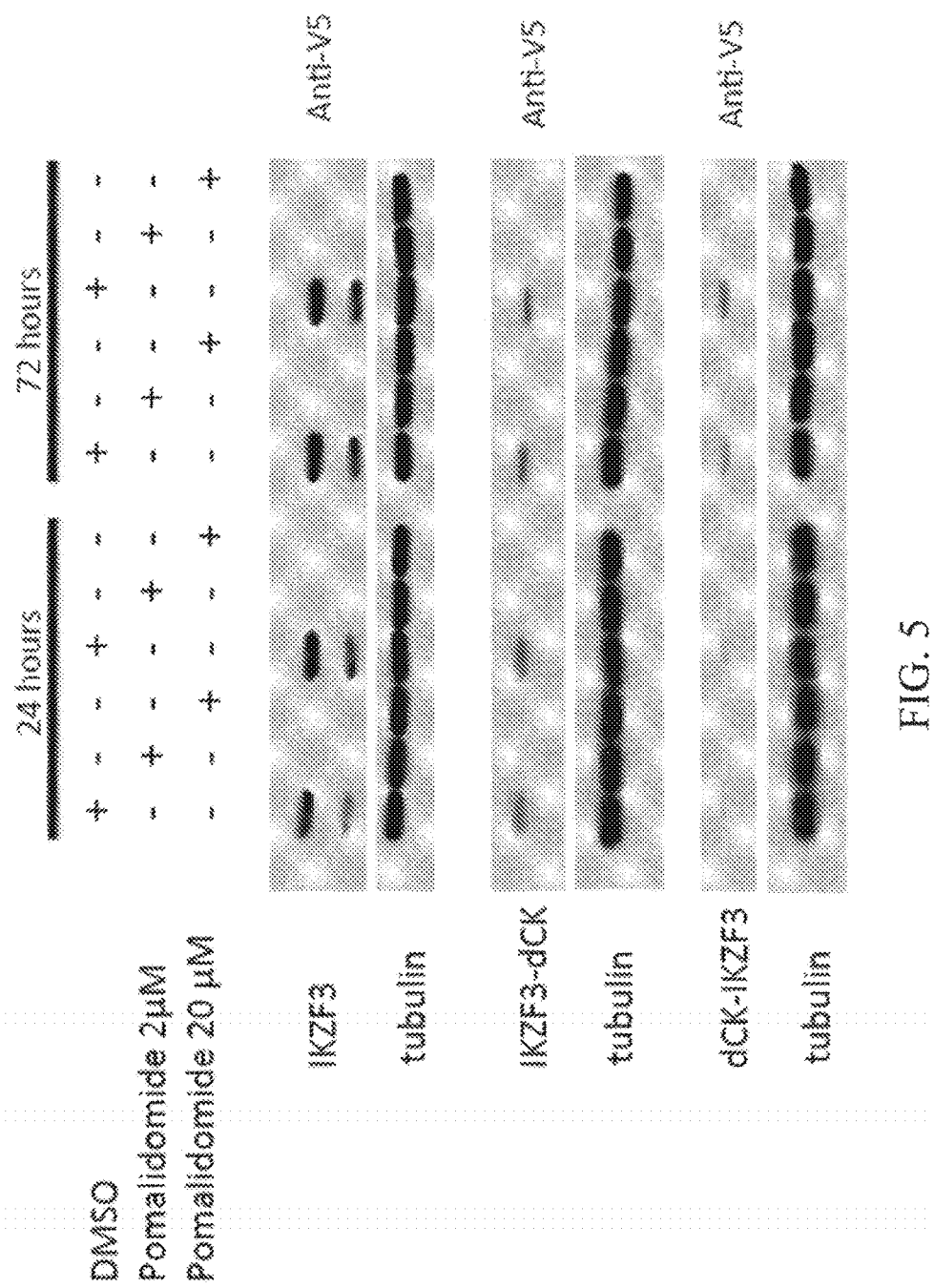
FIG. 5 depicts the effects of pomalidomide on expression of IKZF3 and IKZF3 fusion constructs utilized in certain embodiments of the techniques described herein.

Next, the effects of an IMiD compound (pomalidomide) on the expression levels of the fusion constructs were investigated. On day 0, 250,000 cells were seeded into each of three wells of a 6-well plate. On day 1, the media were replaced with 2 mL of DMEM media supplemented with DMSO (mock), 2 μM or 20 μM Pomalidomide. Cells were washed twice with ice-cold PBS and harvested in EBC Lysis Buffer supplemented with 1× protease inhibitor (Roche). Whole cell extracts were resolved by SDS-PAGE, transferred onto a nitrocellulose membrane, and probed with indicated primary antibodies. Cellular levels of IKZF3 and IKZF3 fusion proteins were shown to be highly sensitive to the IMiD compound pomalidomide (FIG. 5).

Figure 6:
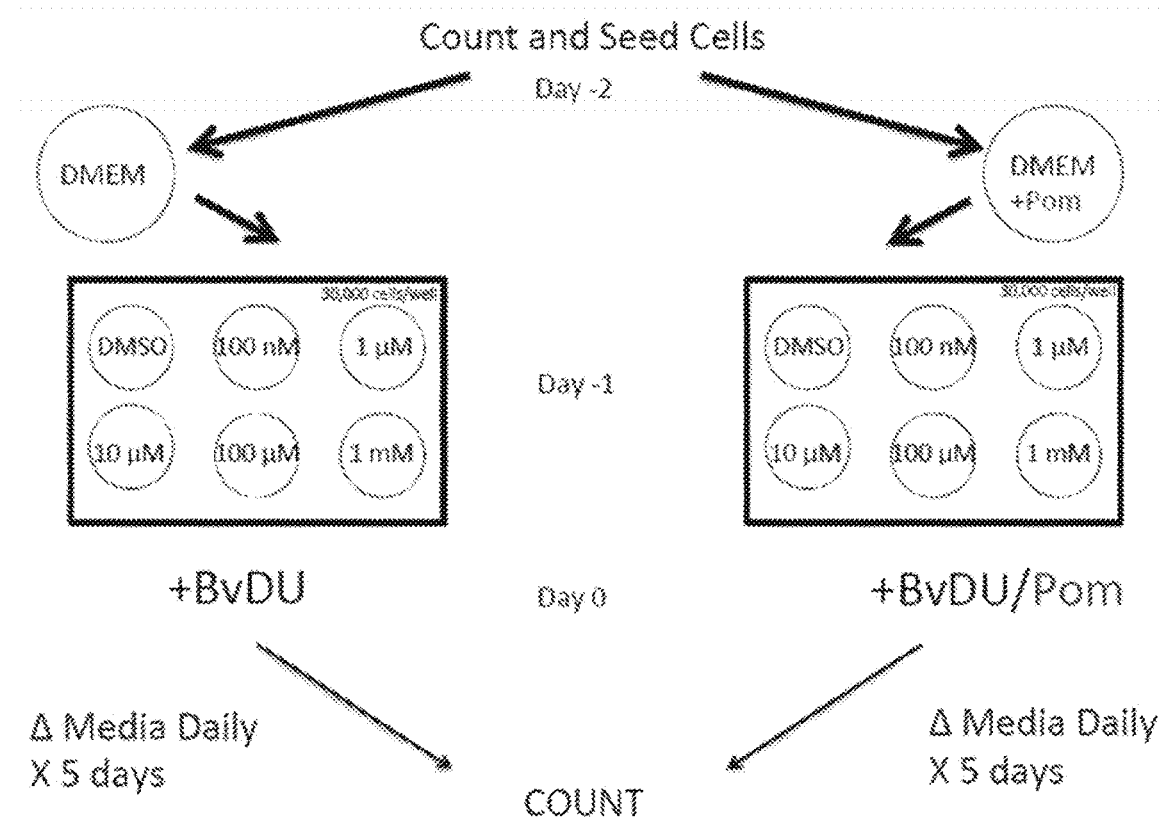
FIG. 6 shows a non-limiting outline of an experimental technique useful for assessing the viability of IKZF positive selection systems, in accordance with some embodiments of the compositions and methods described herein.

To assess the validity of the proposed positive selection system, a set of experiments was devised according to the technique outlined in FIG. 6. On day −2, 1×10$^6$ cells were seeded into a 6 cm dish with 4 mL of DMEM culture media. On day −1, 30,000 cells were seeded per well of a 6 well plate in DMEM media, and on day 0, media were replaced with DMEM media supplemented with decreasing concentrations of BVdU, generated by serial dilution. From days 0-4, media were replaced daily, and on day 5, cells were counted by Vi-Cell. For pomalidomide rescue experiments, the cells were seeded as described above, but from day −2 onwards, were maintained in DMEM media supplemented with 2 μM pomalidomide (Selleck Chemicals).

Figure 7:
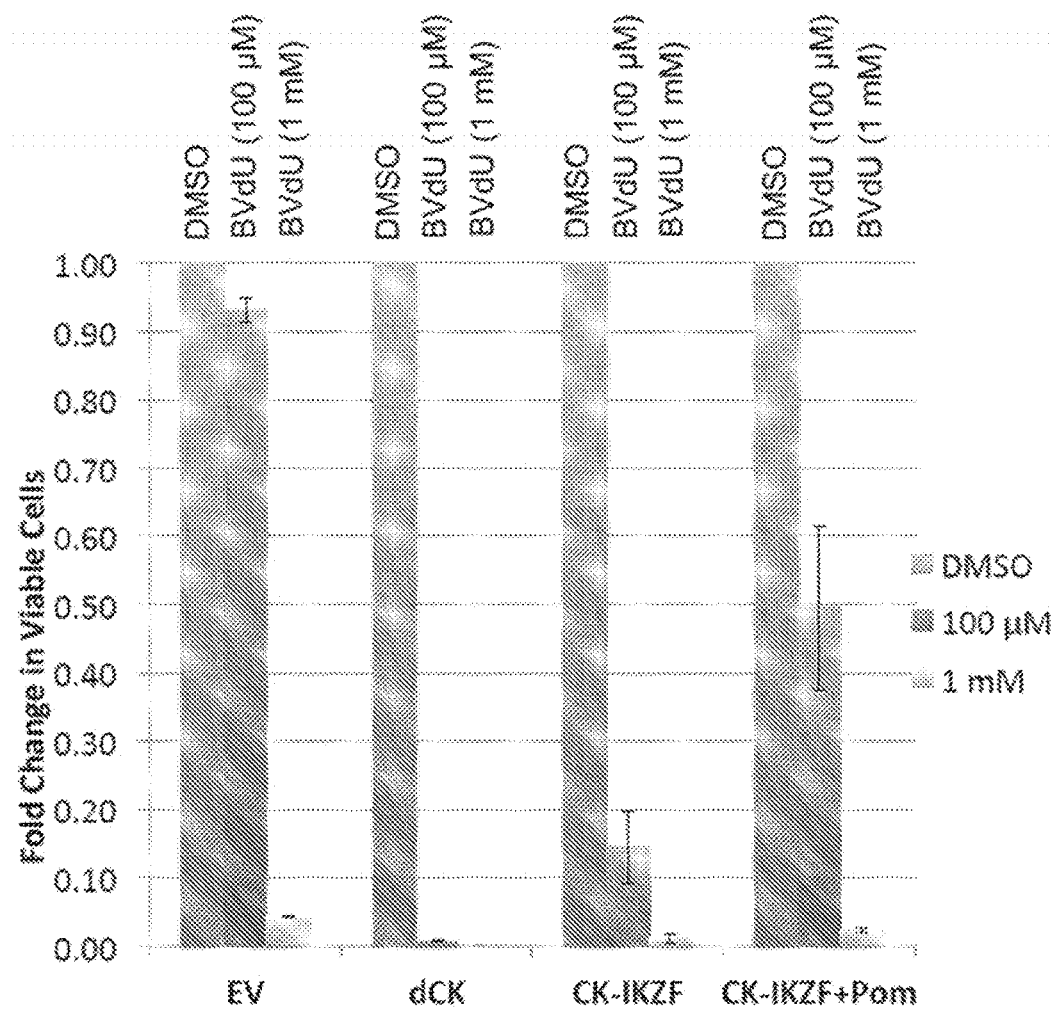
FIG. 7 is a chart showing the change in cell viability of cells expressing various constructs and cultured with differing levels of BVdU, in accordance with some embodiments of the compositions and methods described herein.
Figure 8:
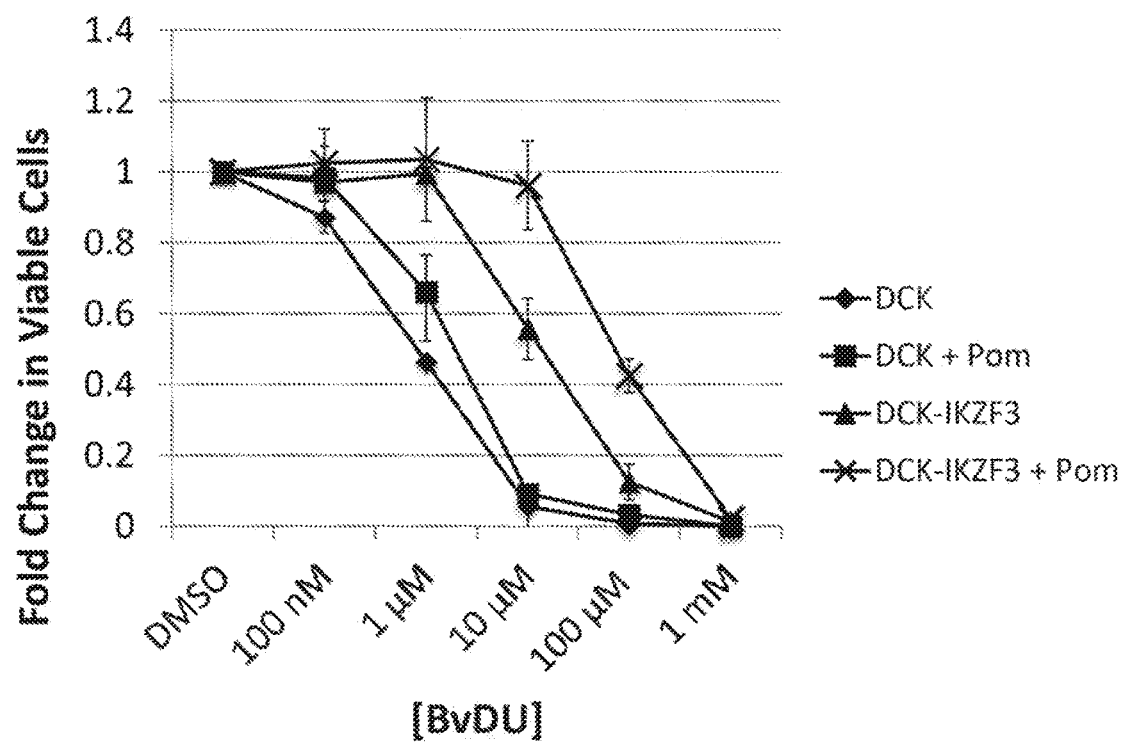
FIG. 8 is a BVdU dose-response curve for cells expressing unfused suicide gene or suicide gene fused to IKZF3, in accordance with some embodiments of the compositions and methods described herein.

As shown in FIG. 7, CK-IKZF3 fusion protein sensitizes cells to BVdU. Cell viability of cells containing a control empty vector ("EV") and cultured in the presence of 100 μM BVdU was nearly unchanged compared to the same cells cultured in the absence of BVdU ("DMSO"). By comparison, cells expressing enzyme ("dCK") and enzyme-protein fusion ("CK-IKZF") showed a drastic reduction in cell viability when cultured with 100 μM BVdU, indicating that the enzyme was active and eliciting cytotoxicity through BVdU turnover. The addition of pomalidomide to cells expressing the fusion construct ("CK-IKZF+Pom") allowed for partial rescue and cell growth. Furthermore, as depicted by the BVdU dose-response curve in FIG. 8, pomalidamide rescue did not occur in cells expressing enzyme only ("DCK+Pom"). Collectively, these results indicate that pomalidomide was selectively targeting the fusion construct for degradation via IKZF3.

Cells expressing the dCK-IKZF fusion protein are used in an up assay that utilizes a test agent in place of pomalidomide. In these experiments, cells having the fusion construct are cultured with BVdU in the presence and absence of a test agent, and cell survival is assessed by examining cell viability and/or any other suitable method. When cells cultured in the presence of the test agent have a greater level of survival and/or viability than cells cultured in the absence of the test agent, the test agent is flagged as an agent of interest that destabilizes the fusion protein. The agent of interest is subjected to further analysis.

To determine whether the agent of interest destabilizes the IKZF portion of the dCK-IKZF fusion protein, cells expressing the unfused dCK enzyme are cultured with BVdU in the presence and absence of the agent of interest, and cell survival is assessed. When the cells cultured in the presence of the agent do not show a significantly greater difference in the level of cell survival and/or viability than the cells cultured in the absence of the agent, the agent of interest is determined to selectively target the IKZF portion of the fusion construct utilized in previous experiments. When a significantly greater difference in the level of cell survival and/or viability is observed, the agent is flagged as being potentially selective toward dCK, and the agent is subjected to further analysis or removed from consideration as an agent of interest that would be selectively destabilizing toward IKZF.

Example 3

Positive Selection of Estrogen Receptor Destabilizers

Fulvestrant is a drug used to treat hormone receptor-positive metastatic breast cancer in postmenopausal women with disease progression following anti-estrogen therapy. It is an estrogen receptor (ER) antagonist that downregulates the ER and has no agonist effects. When fulvestrant binds to ER monomers, it inhibits receptor dimerization, the ER activating function 1 (AF1) and activating function 2 (AF2) domains are rendered inactive, translocation of the receptor to the nucleus is reduced, and degradation of the ER is accelerated.

Figure 9:
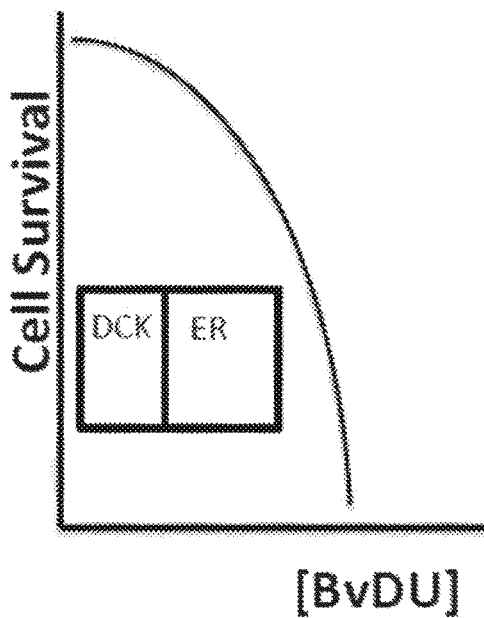
FIG. 9 illustrates positive selection of ER destabilizing agents, in accordance with some embodiments of the compositions and methods described herein.
Figure 9:
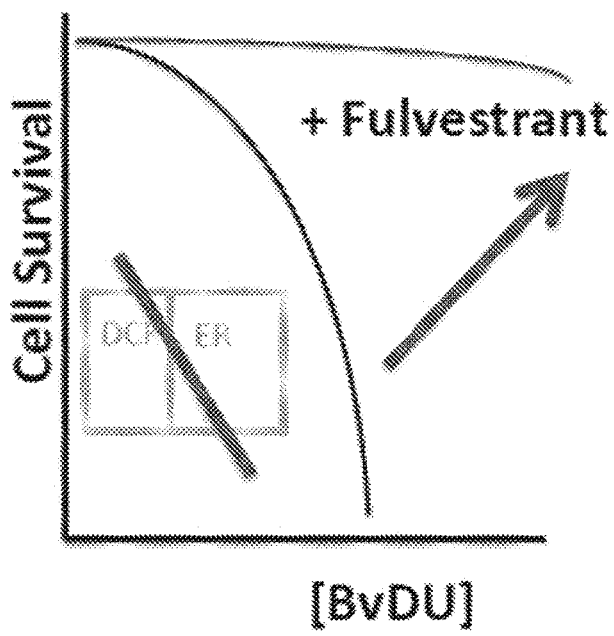

To select for novel molecules having function analogous to fulvestrant, a positive selection system was developed that utilizes a fusion construct having a target protein (ER) and dCK. As in the positive selection system described in Example 2, this technique takes advantage of the ability of dCK to convert a non-toxic substrate (BVdU) into a product that elicits cytotoxicity. Thus, expression of a dCK-ER fusion construct in the presence of increasing concentrations of BVdU would produce a concomitant decrease in cell survival (FIG. 9, top). The addition of an agent with fulvestrant-like properties would presumably result in degradation of the fusion construct having ER, ultimately rescuing the cell from cytotoxicity that would otherwise result from phosphorylated BVdU (FIG. 9, bottom).

Figure 10:
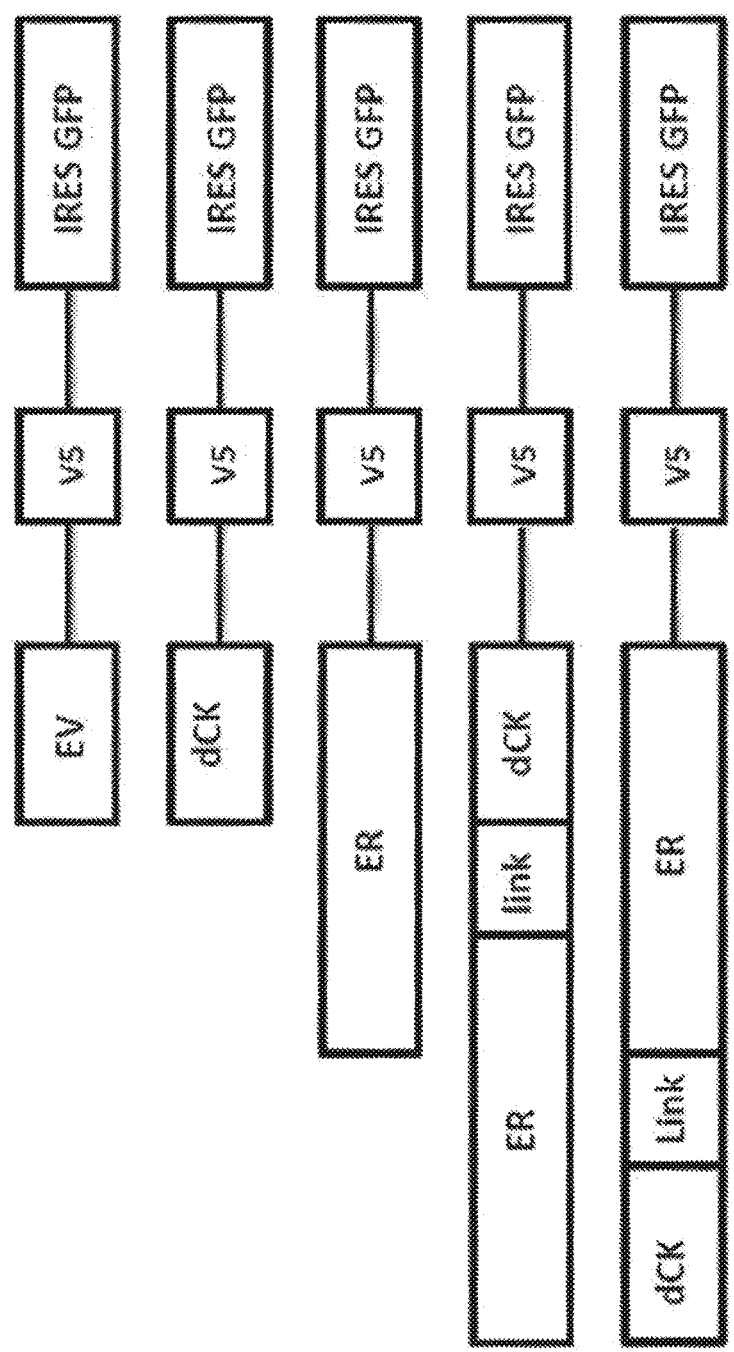
FIG. 10 shows non-limiting constructs useful for positive selection of ER destabilizing agents, in accordance with some embodiments of the compositions and methods described herein.
Figure 11:
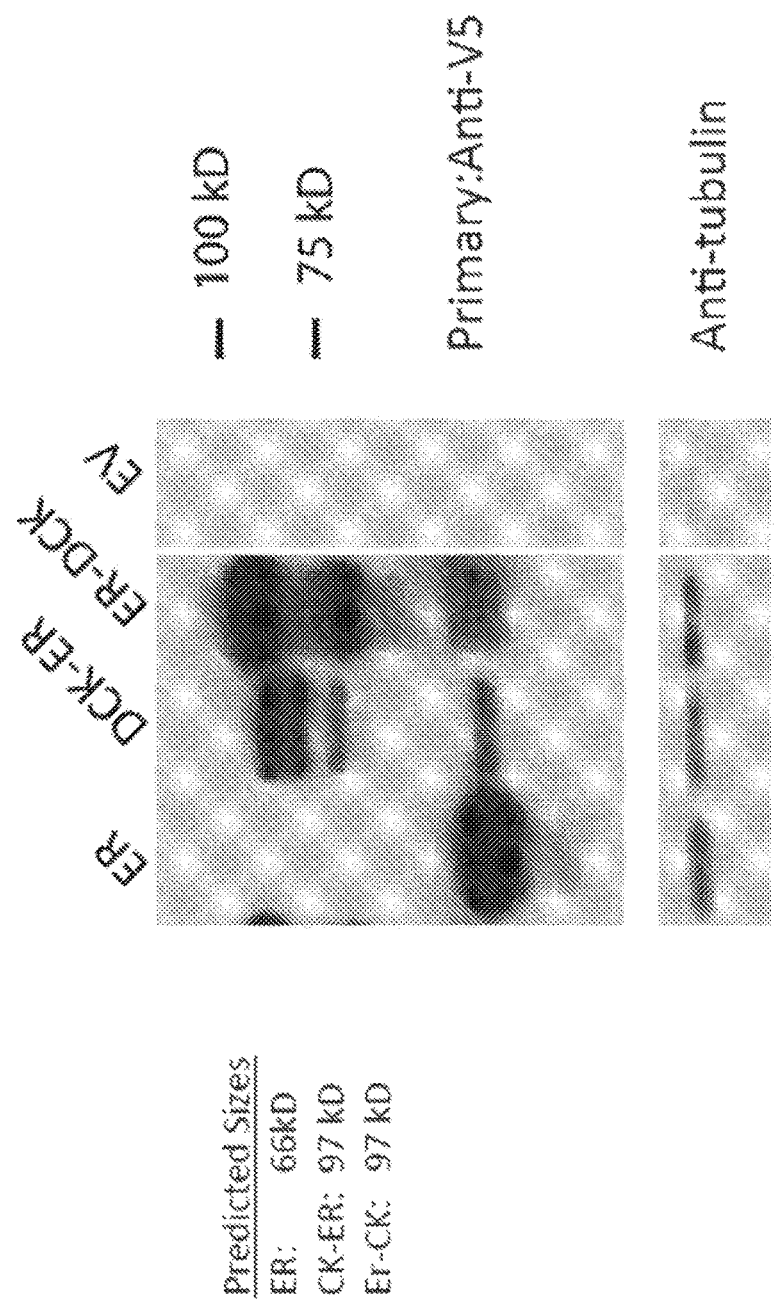
FIG. 11 depicts protein expression, via SDS-PAGE, of control and ER fusion constructs utilized in certain embodiments of the techniques described herein.

Lentiviral expression vectors were designed as depicted in FIG. 10, and selected constructs were obtained by the cloning procedures described above. SDS-PAGE and anti-V5 rabbit polyclonal antibody probes verified expression of the constructs, as shown in FIG. 11.

Figure 12:
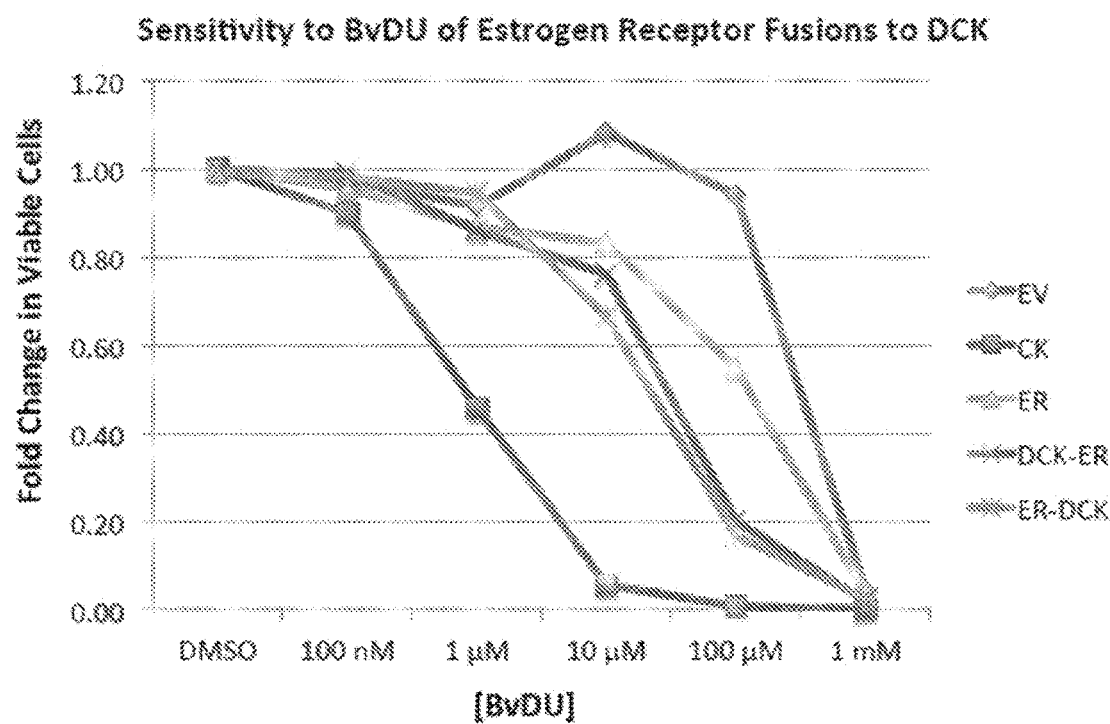
FIG. 12 is a BVdU dose-response curve for cells expressing various ER constructs, in accordance with some embodiments of the compositions and methods described herein.

As shown in FIG. 12, the dCK fusion constructs sensitize cells to BVdU regardless of permutation (DCK-ER and ER-DCK) in a dose-dependent manner. Compared to cells having a control empty vector ("EV"), cells expressing enzyme ("dCK") and enzyme-protein fusion ("DCK-ER," "ER-DCK") showed a drastic reduction in cell viability when cultured with BVdU, indicating that the dCK enzyme was active and eliciting cytotoxicity through BVdU turnover. The addition of fulvestrant to cells expressing the fusion construct may allow for rescue and cell growth.

Cells expressing the dCK-ER or ER-dCK fusion protein are used in an up assay that utilizes a test agent in place of fulvestrant. In these experiments, cells having the fusion construct are cultured with BVdU in the presence and absence of a test agent, and cell survival is assessed by examining cell viability and/or any other suitable method. When cells cultured in the presence of the test agent have a greater level of survival and/or viability than cells cultured in the absence of the test agent, the test agent is flagged as an agent of interest that destabilizes the fusion protein. The agent of interest is subjected to further analysis.

To determine whether the agent of interest destabilizes the ER portion of the dCK-ER/ER-dCK fusion protein, cells expressing the unfused dCK enzyme are cultured with BVdU in the presence and absence of the agent of interest, and cell survival is assessed. When the cells cultured in the presence of the agent do not show a significantly greater difference in the level of cell survival and/or viability than the cells cultured in the absence of the agent, the agent of interest is determined to selectively target the ER portion of the fusion construct utilized in previous experiments. When a significantly greater difference in the level of cell survival and/or viability is observed, the agent is flagged as being potentially selective toward dCK, and the agent is subjected to further analysis or removed from consideration as an agent of interest that would be selectively destabilizing toward ER.

Example 4

Additional Fusion Systems

Figure 13A:
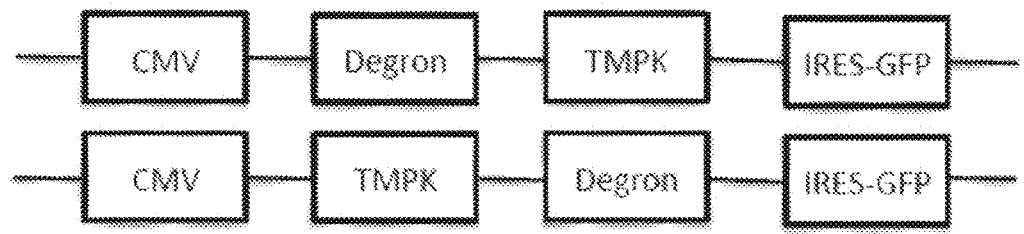
FIG. 13A shows non-limiting constructs useful for positive selection of thymidylate kinase destabilizing agents, in accordance with some embodiments of the compositions and methods described herein.
Figure 13B:
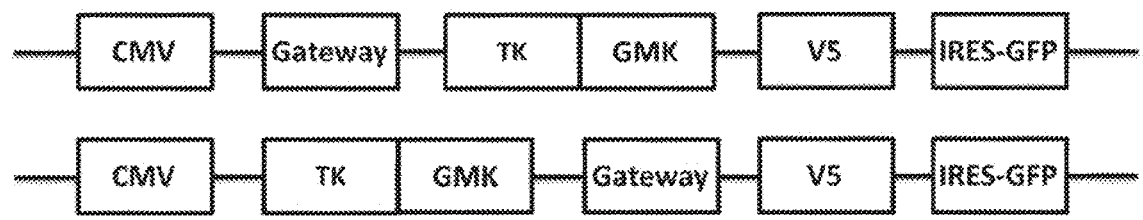
FIGS. 13B and 13C show non-limiting constructs useful for positive selection of protein destabilizing agents, in accordance with some embodiments of the compositions and methods described herein.
Figure 13C:
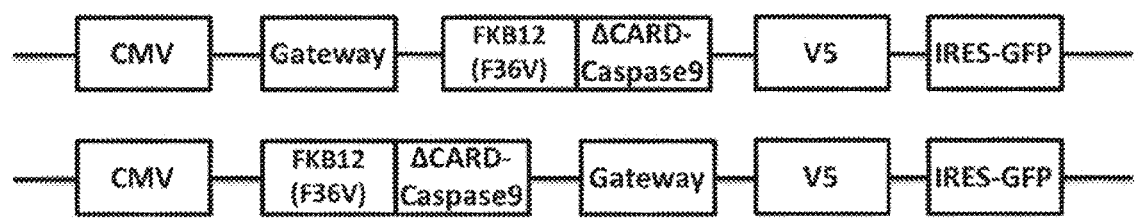

The assays described herein may be performed using other cytotoxic genes, such as the fusion systems depicted in FIGS. 13A-13C. These constructs are based on techniques relating to suicide gene therapy of cancer (SGTC), also termed gene-directed enzyme-prodrug therapy (GDEPT). These techniques typically rely on the intratumoral delivery of suicide genes that facilitate selective and localized activation of specific prodrugs into their cytotoxic effector derivatives (see, e.g., Sato, et al. (2007) Mol Ther 15: 962-970; Ardiani, et al. (2010) Cancer Gene Therapy 17(2): 86-96; Ramos, et al. (2010) Stem Cells 28(6): 1107-1115; the contents of each of which are hereby incorporated by reference).

The construct shown in FIG. 13A utilizes an engineered variant of human thymidylate kinase (TMPK), which may be fused to a POI and expressed in cells in the presence of the prodrug 3'-azido-3'-deoxythymidine (AZT). AZT may be converted through phosphorylation into the cytotoxic derivative AZT-triphosphate (AZT-TP). The rate-limiting step in the conversion of AZT to the cytotoxic AZT-TP form is the phosphorylation of AZT-monophosphate to AZT-diphosphate, which is catalyzed by the engineered TMPK variant. Thus, if a test agent destabilizes a POI fused to TMPK in cells being cultured in the presence of AZT, the resulting cell survival may be used to positively identify the test agent as destabilizing toward the POI.

The construct shown in FIG. 13B utilizes a thymidine kinase-guanylate kinase (TK-GMK) fusion pair, which may be fused to a POI and expressed in cells in the presence of the synthetic guanosine analog, ganciclovir. Ganciclovir may be endogenously converted into its cytotoxic triphosphate form via independent and successive phosphorylation events catalyzed by the TK-GMK fusion pair. Thus, if a test agent destabilizes a POI fused to TK-GMK in cells being cultured in the presence of ganciclovir, the resulting cell survival may be used to positively identify the test agent as destabilizing toward the POI.

The construct shown in FIG. 13C utilizes a proapoptotic gene product, iCasp9, which may be fused to a POI and expressed in cells in the presence of a chemical inducer of dimerization (CID), such as AP1903. The CID functions by binding to a FK506-binding domain (FKB12) present in iCasp9 and inducing FKB12 dimerization, which activates Caspase 9 ($\Delta$CARD-Caspase9) to elicit cytotoxicity. Thus, if a test agent destabilizes a POI fused to FKB12-$\Delta$CARD-Caspase9 in cells being cultured in the presence of a CID, the resulting cell survival may be used to positively identify the test agent as destabilizing toward the POI.

Example 5

Cell Mixtures as Positive Selection Systems

Mixing studies were conducted to investigate the use of cell mixtures as positive selection systems. Further to the concepts and constructs described in the above examples, competition assays were designed that utilize cell outgrowth to positively identify protein destabilizing agents. Preliminary experiments were performed to investigate the bystander effect in cell mixtures. The bystander effect involves the propagation of cytotoxicity from a cell transfected with a toxic gene to a nearby cell that has not been transfected with a toxic gene. Significant bystander killing, if present, could confound the interpretation of pooled positive selection assays.

Figure 14:
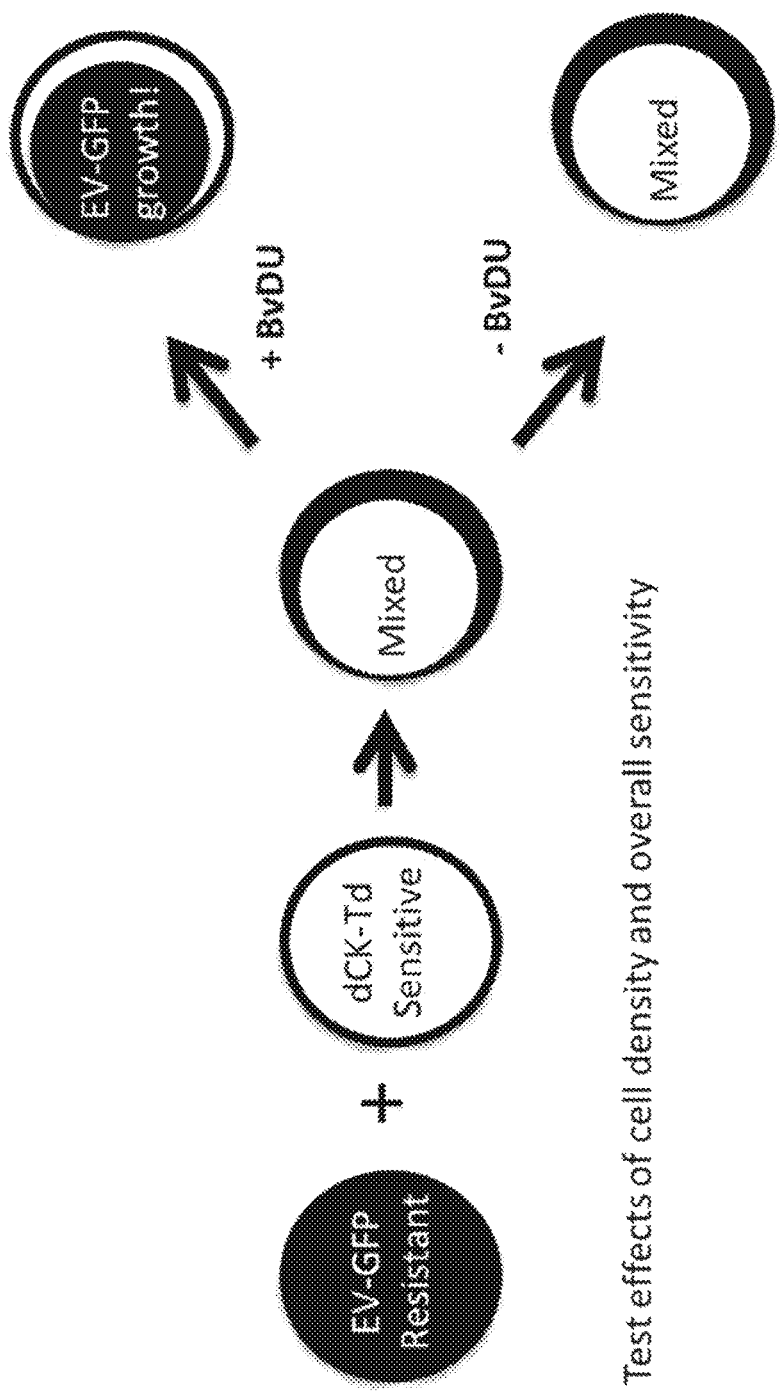
FIG. 14 illustrates a non-limiting scheme of cell mixing studies performed using cells resistant to BVdU and cells sensitive to BVdU, in accordance with some embodiments of the compositions and methods described herein.

The scheme depicted in FIG. 14 generally describes the bystander effect assay in the context of dCK positive selection systems. Cells expressing dCK and tomato fluorescent protein (Td) are mixed with cells having empty vector (EV) and green fluorescent protein (GFP). When cultured with BVdU, cells expressing dCK are expected to convert the nucleotide analog into a product that elicits cytotoxicity, resulting in outgrowth of resistant cells (EV-GFP) as measured by relative GFP/Td fluorescence in the absence of significant bystander killing.

Figure 15:
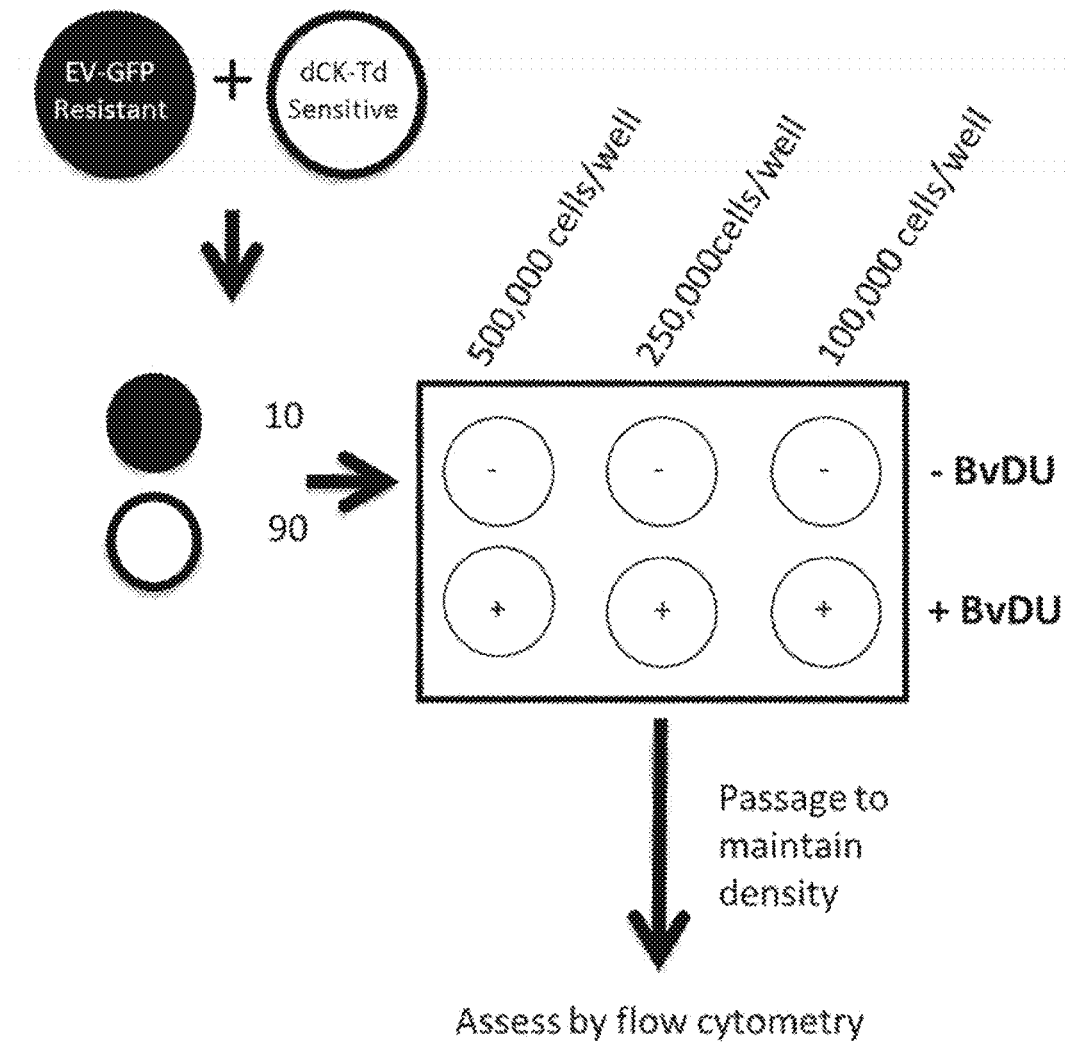
FIG. 15 shows a non-limiting outline of an experimental technique useful for assessing bystander-mediated cell death, in accordance with some embodiments of the compositions and methods described herein.

The effects of cell density in cell mixture experiments were examined. EV-GFP cells were mixed together with dCK-Tomato cells in a ratio of 1:9, and the resulting mixture of cells was plated in 6 well plates at 500,000 cells/well, 250,000 cells/well, and 100,000 cells/well, with two wells plated per cell density (FIG. 15). For each cell density, one well received 100 µM BVdU, and the other an equivalent amount of DMSO. Cells were split and re-seeded every 72 hours, to preserve cell density, and analyzed by flow cytometry to quantify the fraction of GFP and Tomato-labeled cells.

Figure 16:
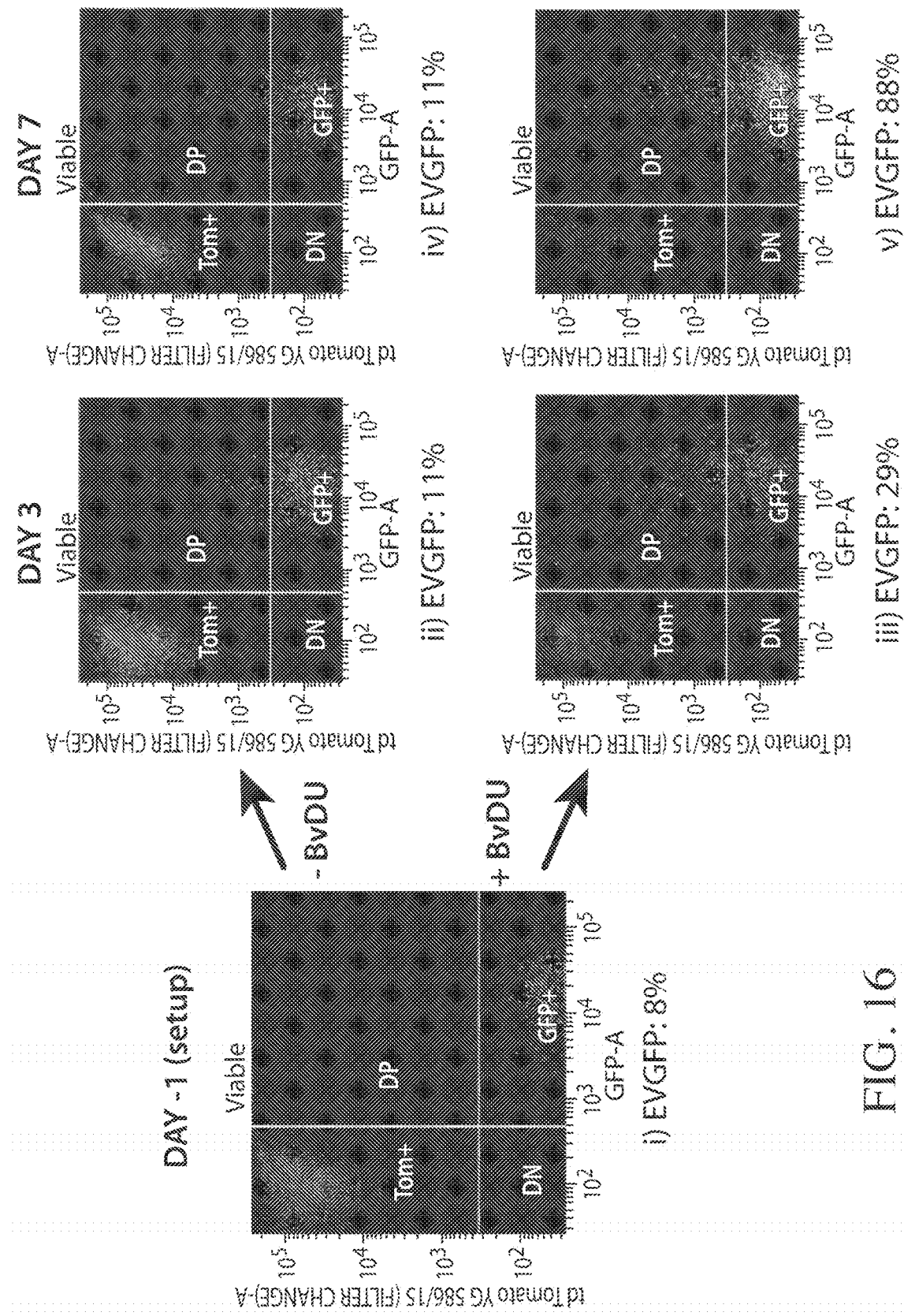
FIG. 16 depicts fluorescence imaging of GFP-expressing cells and tdTomato-expressing cells cultured in the presence and absence of BVdU, in accordance with some embodiments of the compositions and methods described herein.

Fluorescence imaging from cell density experiments (100,000 cells/well) is shown in FIG. 16. On day −1, EV-GFP signals (i, bottom right quadrant of FACS plots depicted in FIG. 16) and dCK-Td signals (i, top left quandrant of FACS plots depicted in FIG. 16) indicated that the resistant cells (EV-GFP) were present at 8% in the cell mixture. Cell mixtures cultured in the absence of BVdU (ii, iv) showed minimal change in EV-GFP percentage by day 7 of the observation period. Cells cultured in the presence of BVdU showed a gradual shift over this period toward EV-GFP outgrowth, with EV-GFP cells constituting 29% of the cell mixture by day 3 (iii) and 88% of the cell mixture by day 7 (v).

Figure 17:
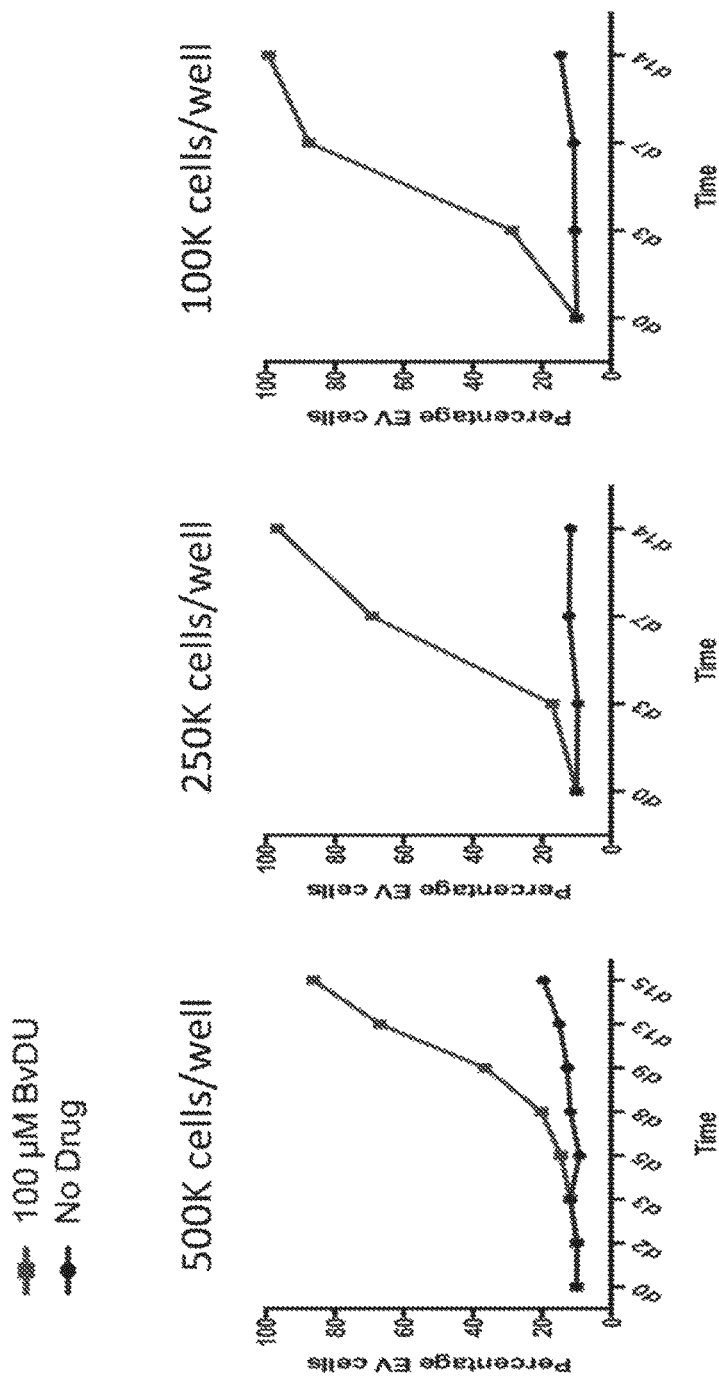
FIG. 17 illustrates the effect of cell density on outgrowth of GFP-expressing cells cultured in the presence and absence of BVdU, in accordance with some embodiments of the compositions and methods described herein.
Figure 18:
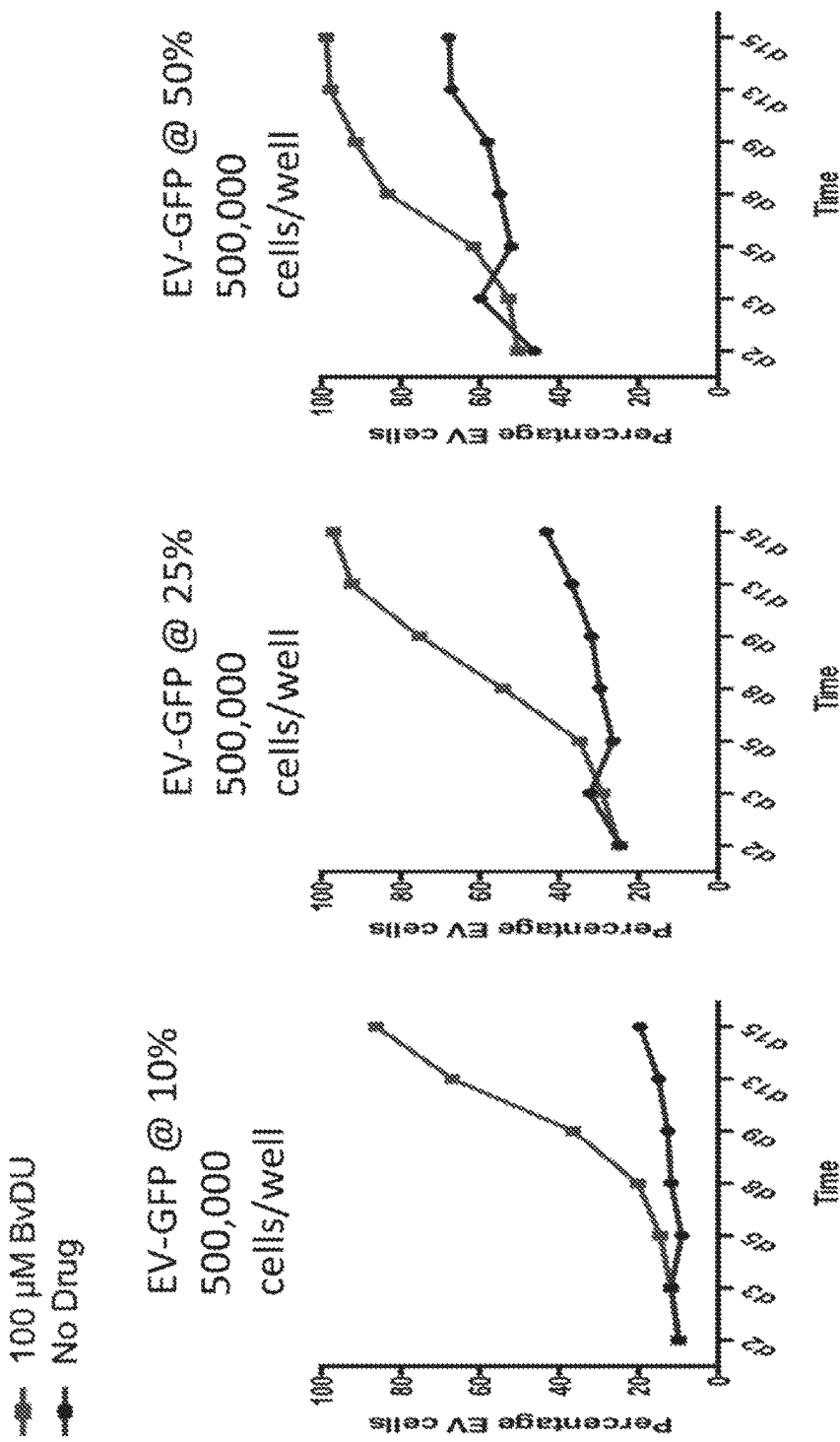
FIG. 18 shows the effect of initial EV-GFP:td-dCK ratio on outgrowth of GFP-expressing cells cultured in the presence and absence of BVdU, in accordance with some embodiments of the compositions and methods described herein.

The observed EV-GFP outgrowth was enhanced at lower cell densities (FIG. 17). The apparent lag in EV-GFP outgrowth in mixtures grown at higher cell densities could be indicative of a bystander effect, wherein the closer proximity of adjacent cells lends itself to propagation of cytotoxic signals. This effect was further investigated by plating cell mixtures at a density of 500,000 cells/well with starting EV-GFP:dCK-Td ratios of 1:9, 1:3, and 1:1 (FIG. 18). Despite the high cell density, EV-GFP cells eventually achieved outgrowth.

Figure 19:
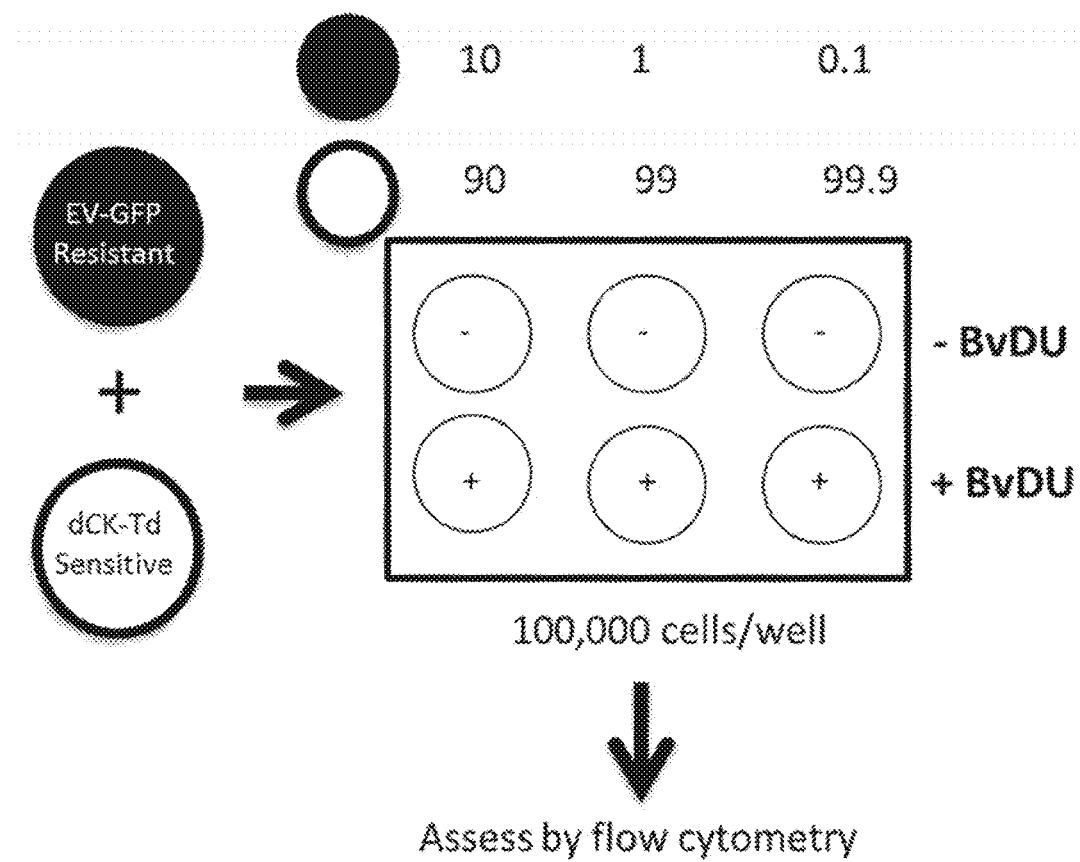
FIG. 19 shows a non-limiting outline of an experimental technique useful for assessing the effect of initial cell:cell ratio in cell mixtures, in accordance with some embodiments of the compositions and methods described herein.
Figure 20:
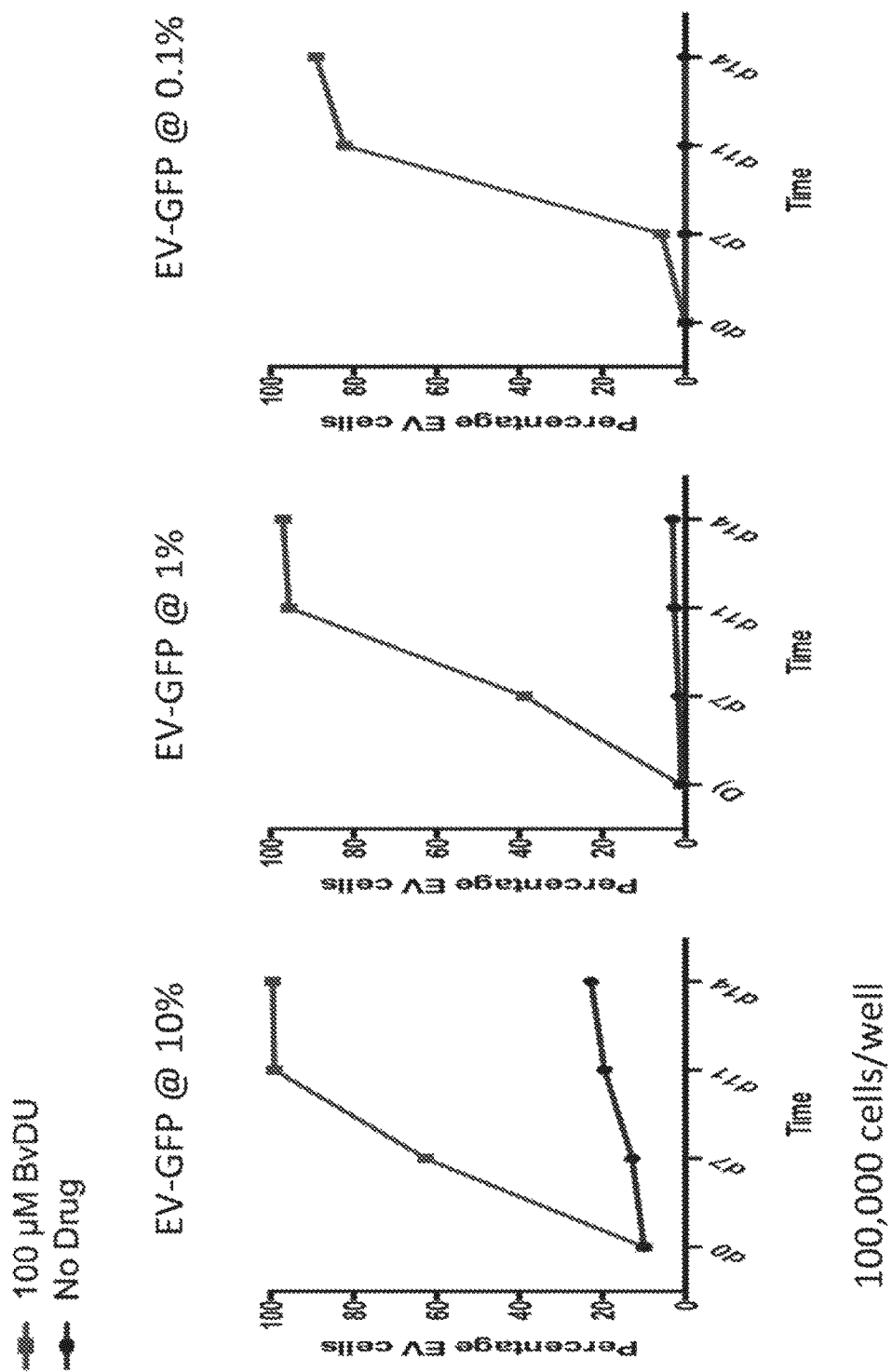
FIG. 20 shows the effect of initial EV-GFP:td-dCK ratio down to 0.1% on outgrowth of GFP-expressing cells cultured in the presence and absence of BVdU, in accordance with some embodiments of the compositions and methods described herein.

The sensitivity of the cell mixture assay was assessed with mixtures plated at 100,000 cells/well and different initial EV-GFP:dCK-Td ratios (FIG. 19). It was postulated that lower levels of bystander-mediated death should allow growth of EV-GFP cells (resistant) and an increase in the GFP/Td signal ratio. EV-GFP cells were mixed together with dCK-Tomato cells in ratios of 1:9, 1:99, and 1:99.9 and plated in 6 well plates at a fixed density of 100,000 cells/well, with two wells/condition. For each ratio of cells, one well received 100 µM BVdU, and the other an equivalent amount of DMSO. Cells were split and re-seeded to maintain cell density every 72 hours, and flow cytometry was used to quantify the fraction of GFP and Tomato-labeled cells. As illustrated by the charts in FIG. 20 depicting EV-GFP outgrowth, the positive selection assay can rescue as few as 0.1% positive EV-GFP cells.

Figure 21:
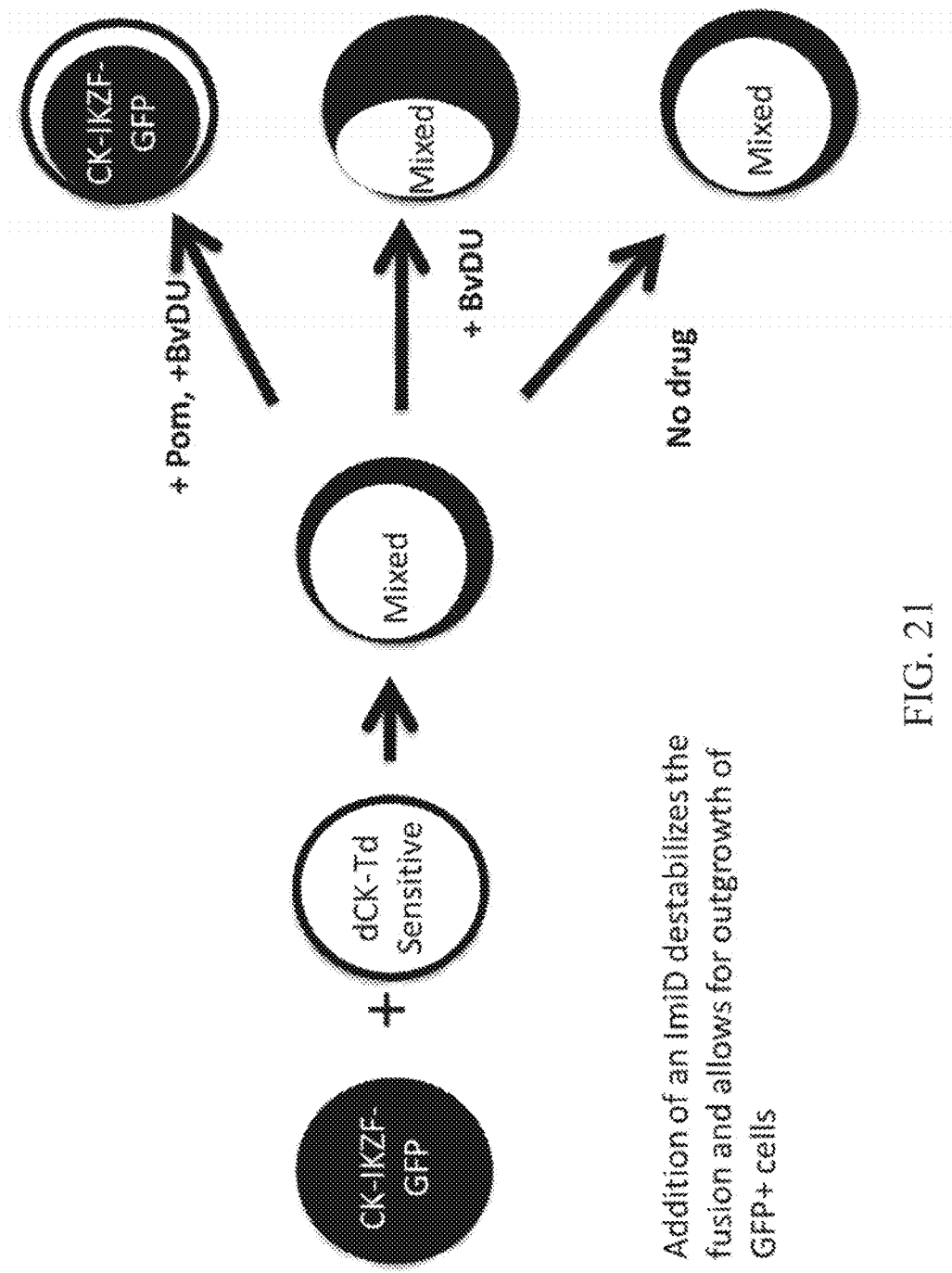
FIG. 21 illustrates a non-limiting scheme of cell mixing studies useful for positive selection of IKZF destabilizing agents, in accordance with some embodiments of the compositions and methods described herein.

Next, a competition assay was devised using dCK and CK-IKZF constructs (FIG. 21). In these experiments, cells expressing dCK-IKZF fusion protein and GFP were mixed with cells expressing dCK and tdTomato. In the presence of BVdU, cells expressing either construct would be capable of generating the cytotoxic product. However, upon the addition of an IMiD (pomalidomide), dCK-IKZF fusion protein would be destabilized, allowing outgrowth of GFP+ cells. dCK-IKZF3 cells labeled with GFP were mixed with dCK cells labeled with tdTomato at a ratio of 1:99 and on day −2, were plated into 6 well plates at 100,000 cells/well in triplicate. On Day −1, the "Mock" and "BVdU" wells were treated with DMSO, and the "pomalidomide" well was treated with 2 µM pomalidomide. On day 0, the "Mock" well was treated with DMSO, while the "BVdU" well was treated with 100 µM BVdU, and the "pomalidomide" well received 2 µM pomalidomide and 100 µM BvDU. Cells were split, re-seeded to maintain cell density, treated with the appropriate drugs and analyzed by flow cytometry every 3 days.

Figure 22:
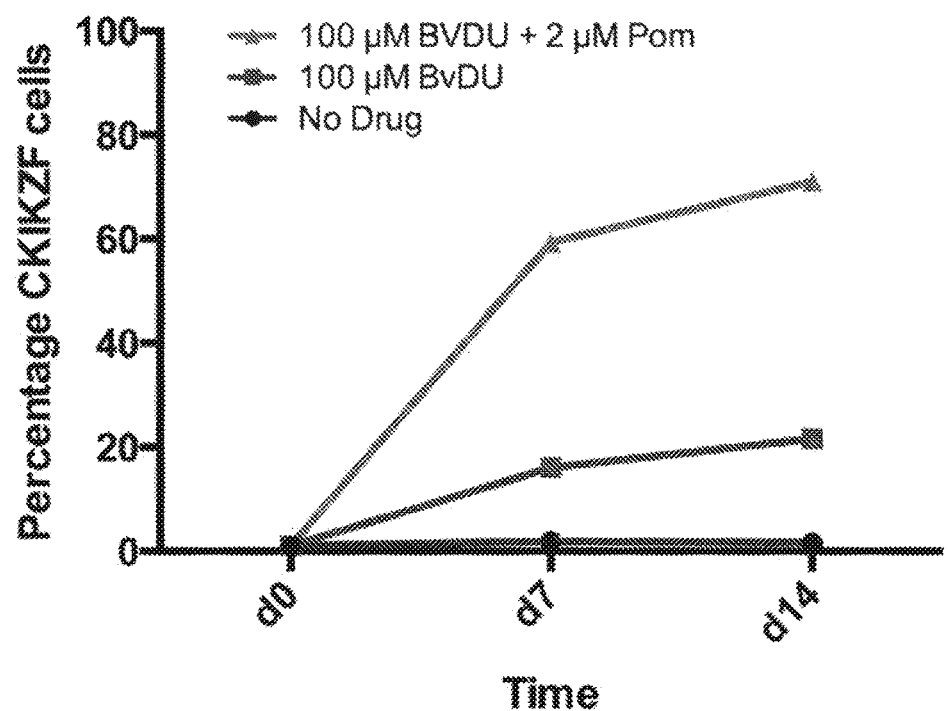
FIG. 22 is a non-limiting chart showing that pomalidomide can rescue a 1% population of IKZF3 fusion-expressing cells cultured over a period of 14 days.

As shown in FIG. 22, pomalidomide rescue experiments validated the cell mixture technique as a viable positive selection system. In cell mixtures having only 1% initial dCK-IKZF3 cells in the mixture, pomalidomide allowed for outgrowth of GFP+cells, indicating destabilization of the dCK-IKZF3 fusion protein. The slight enrichment of the CK-IKZF3 cells in the presence of BVdU and absence of POM is expected based on the steady-state levels of CK-IKZF and dCK shown in FIG. 4.

A cell mixture having a first portion of cells expressing dCK-IKZF fusion protein and GFP and a second portion of cells expressing dCK and tdTomato are used in an up assay that utilizes a test agent in place of pomalidomide. In these experiments, the cell mixture contains a known relative amount of each portion of cells and is cultured with BVdU in the presence of a test agent, and cell survival of the portions is assessed by detecting relative GFP/Td fluorescence signals. If the cell mixture indicates a greater relative population of GFP+ cells in the cultured cell mixture compared to the relative population of GFP+ cells prior to culturing, the test agent is flagged as an agent of interest that destabilizes the IKZF fusion protein. Alternatively, the cell mixture can be separately cultured in the absence of the test agent. When cell mixtures cultured in the presence of the test agent have a greater level of GFP+outgrowth compared to cell mixtures cultured in the absence of the test agent, the test agent is flagged as an agent of interest that destabilizes the IKZF fusion protein. The agent of interest is subjected to further analysis.

Example 6

"Up" Assay Correctly Identifies IMiDs from a Drug Library

Figure 23:
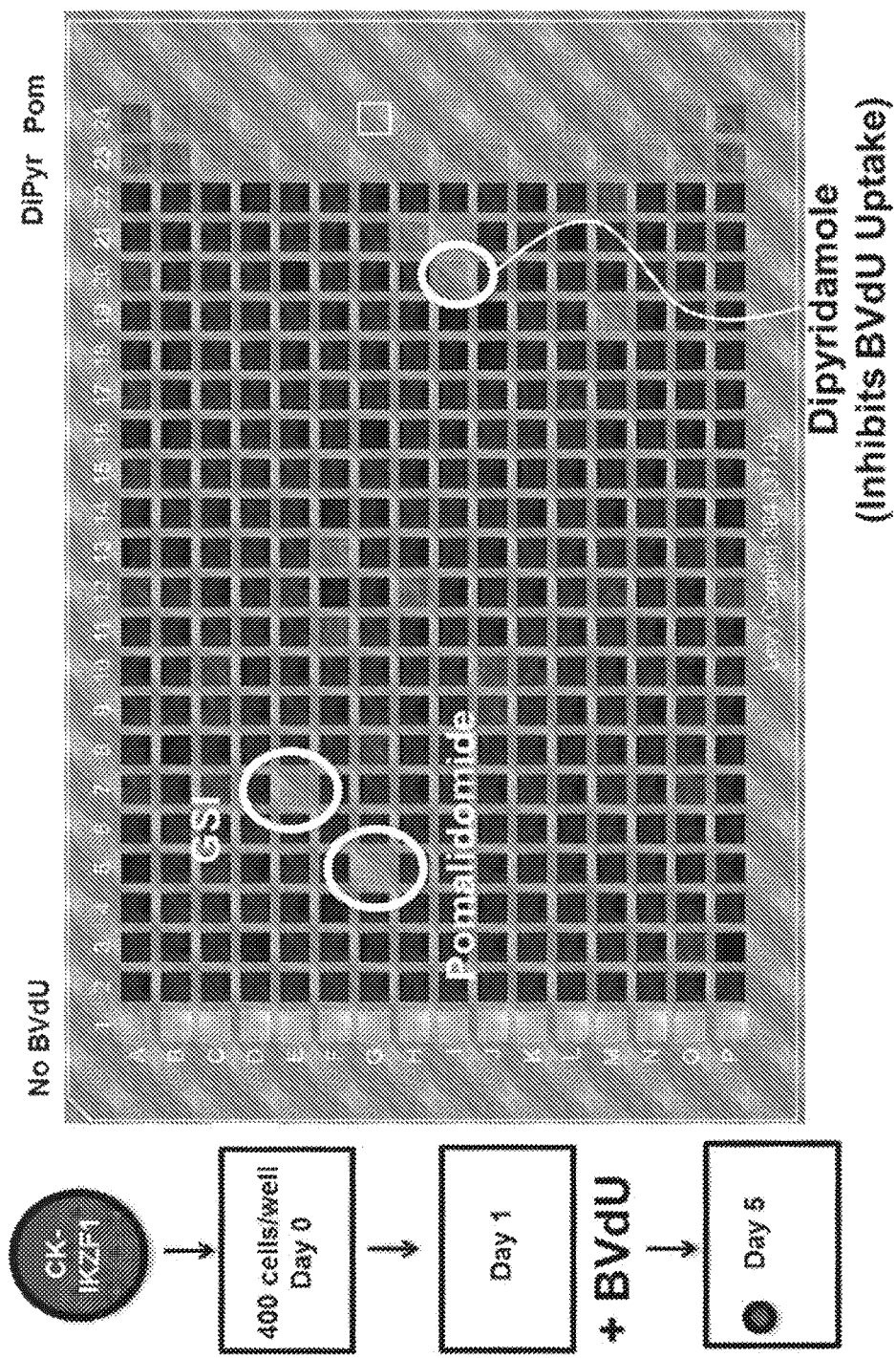
FIG. 23 depicts a workflow (left) for a pilot drug screen that was conducted in multi-well plates. Raw GFP fluorescence data is further shown from a representative plate (right).

A pilot drug screen in multi-well format was conducted, as depicted in the workflow shown in FIG. 23 (left). As shown, 293T cells stably infected to produce DCK-IKZF1-IRES-GFP were seeded in 384 well plates on Day 0. Columns 1, 23, and 24 of the plate shown in FIG. 23 (right) were treated with DMSO, Pomalidomide, and Dipyridamole, respectively, while each well in Columns 2-22 was treated with an individual drug (concentration=~25 µM) from a library of approximately 550 bioactive chemicals. On Day 1, Column 1 was treated with DMSO, and Columns 2-24 were treated with BVdU. On Day 5, GFP fluorescence in each well was quantified using an Acumen Laser Cytometer. Raw GFP fluorescence data is shown from a representative plate (FIG. 23, right).

Figure 24:
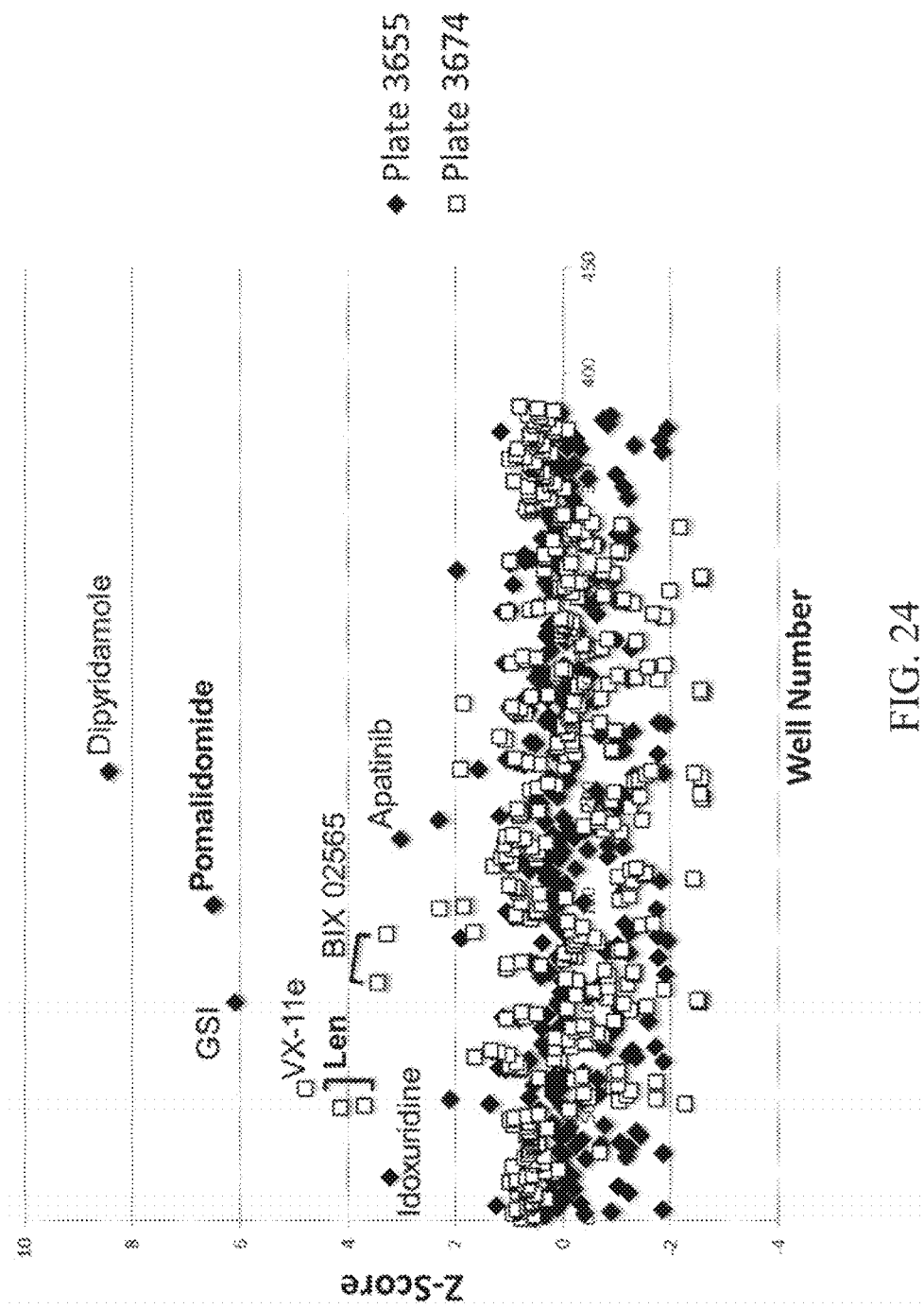
FIG. 24 is a plot depicting true-positive hits and non-specific hits resulting from the drug screen illustrated in FIG. 23. The plot was generated by converting GFP fluorescence data for each well on a given plate into a Z-statistic.

GFP fluorescence data for each well on a given plate was converted into a Z-statistic and plotted to display both true-positive hits as well as non-specific hits (FIG. 24). As shown, true-positive hits included Pomalidomide and Lenalidomide, and non-specific hits included "GSI" and dipyridamole. Non-specific hits are those that are "assay positives," or hits that score irrespective of CK fusion partner.

Example 7

Comparison of "Up" and "Down" Assays Using a Limited Drug Library

Figure 25:
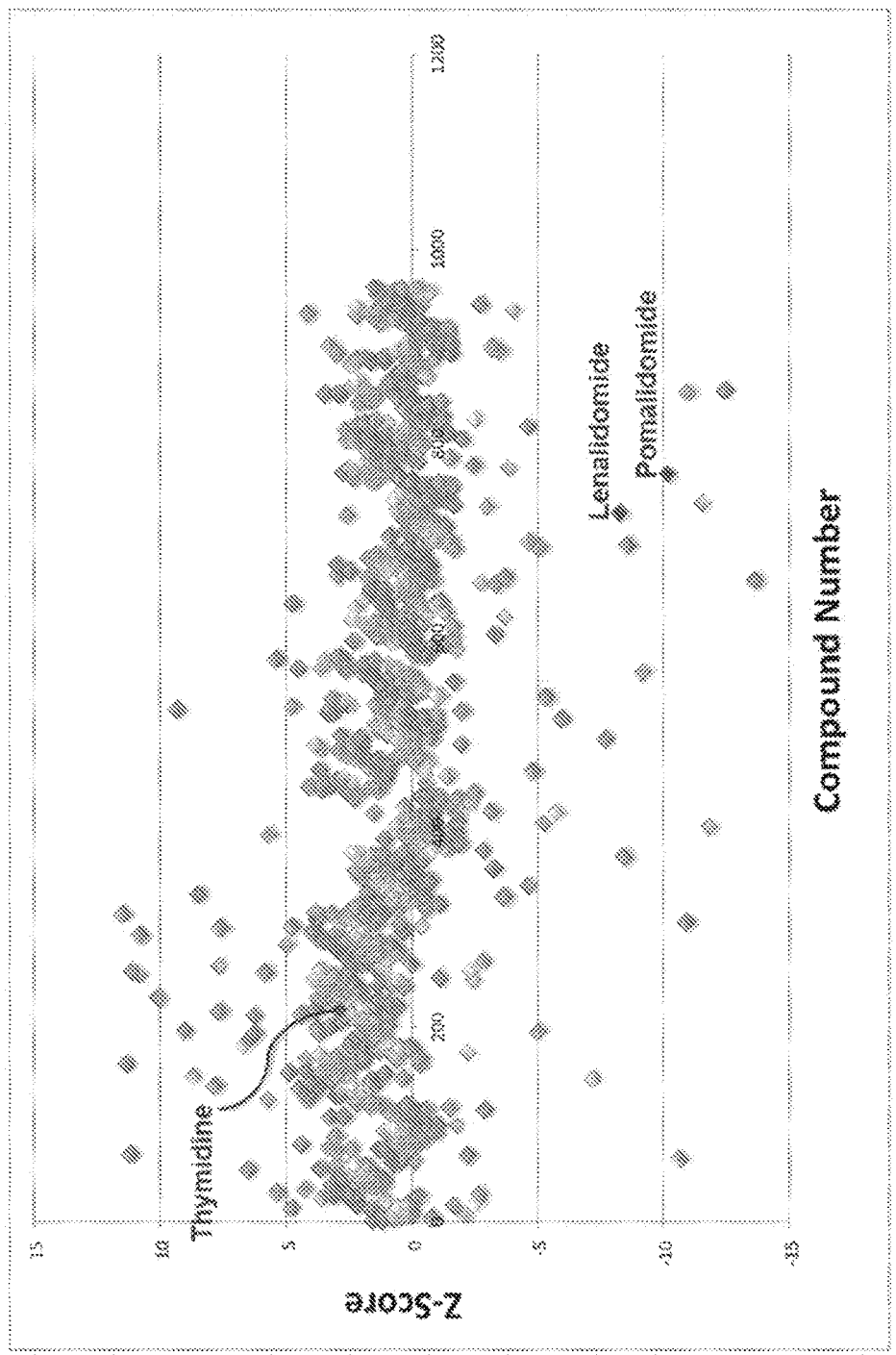
FIG. 25 is a plot of GFP fluorescence data, from an "up" assay, converted to a Z-statistic to highlight both true-positive hits and non-specific hits.

A comparative assessment of "up" and "down" assays was performed using a limited drug library of approximately 700 compounds, including Pomalidomide and Lenalidomide. For the up assay experiment, 293T cells stably infected to produce DCK-IKZF1-IRES-GFP were seeded in three 384 well plates on Day 0. Each well on each plate received a library drug from a ~700 compound drug library, and BVdU on Day 2. GFP fluorescence in each well was quantified on Day 5, and for each plate, GFP fluorescence data was converted to a Z-statistic and plotted to highlight both true-positive hits (Pomalidomide, Lenalidomide) as well as non-specific hits that are "assay positives" (FIG. 25).

Figure 26:
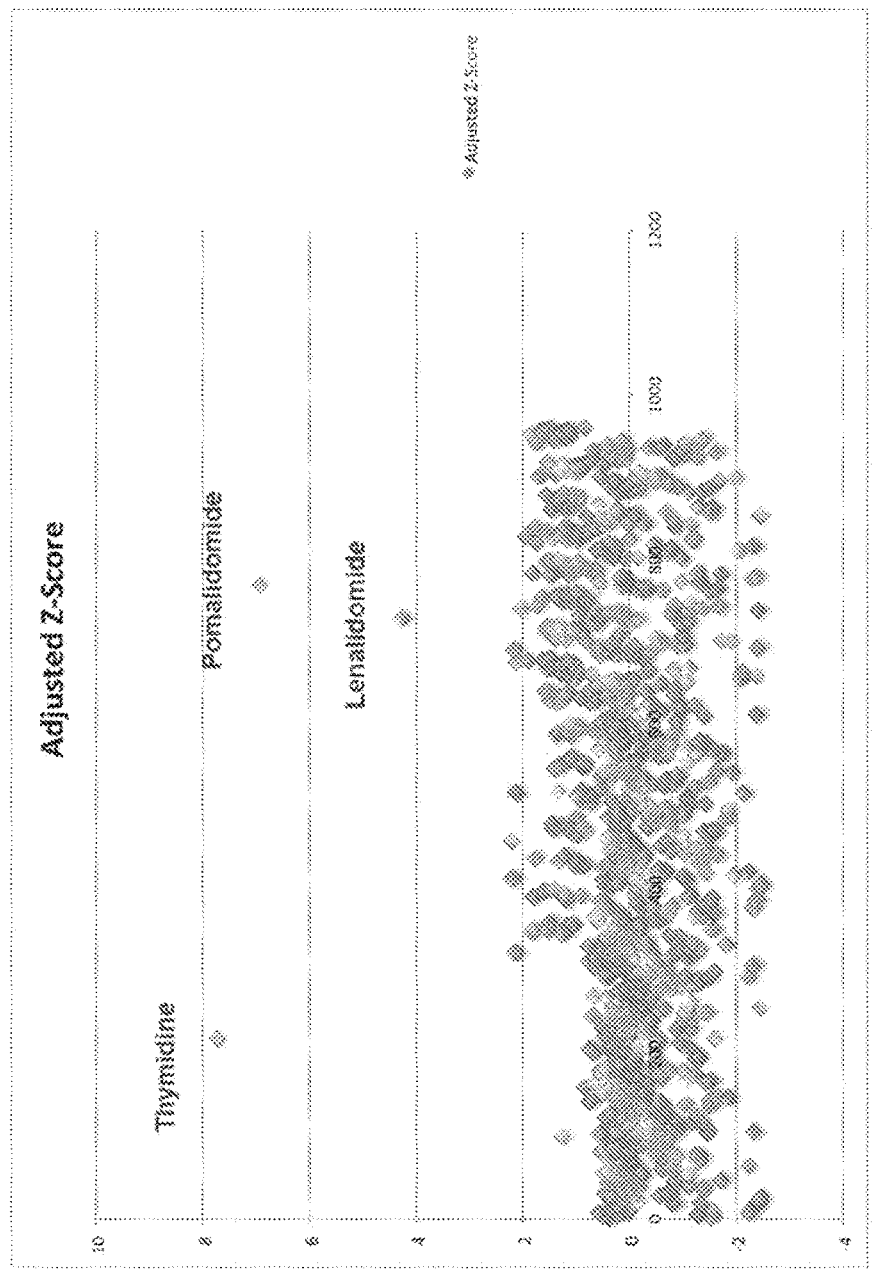
FIG. 26 is a plot of GFP fluorescence data, from a "down" assay, converted to a Z-statistic to highlight both true-positive hits and non-specific hits.

A down assay experiment was conducted in parallel with the up assay experiment. For the down assay experiment, 293T cells stably infected to produce the IKZF1-Firefly luciferase protein as well as the Renilla luciferase protein from a single mRNA transcript were treated as described in the "Up" Assay. On Day 5, for each plate, Firefly and Renilla luciferase signals were quantified, and the Firefly/Renilla ratio calculated for each well and converted to a Z-statistic and plotted (FIG. 26). The hits noted in the "Up Assay" have been labeled in FIG. 25 and FIG. 26 to allow for comparison between the two assays. It was determined that Pomalidomide and Lenalidomide are "True Positive" hits, while Thymidine is an assay positive in the "Up" Assay that interferes with BVdU-mediated cell death, but which does not score in the "Down" Assay.

Example 8

Distinguishing True Positives from Assay Positives in the Same Well

Figure 27:
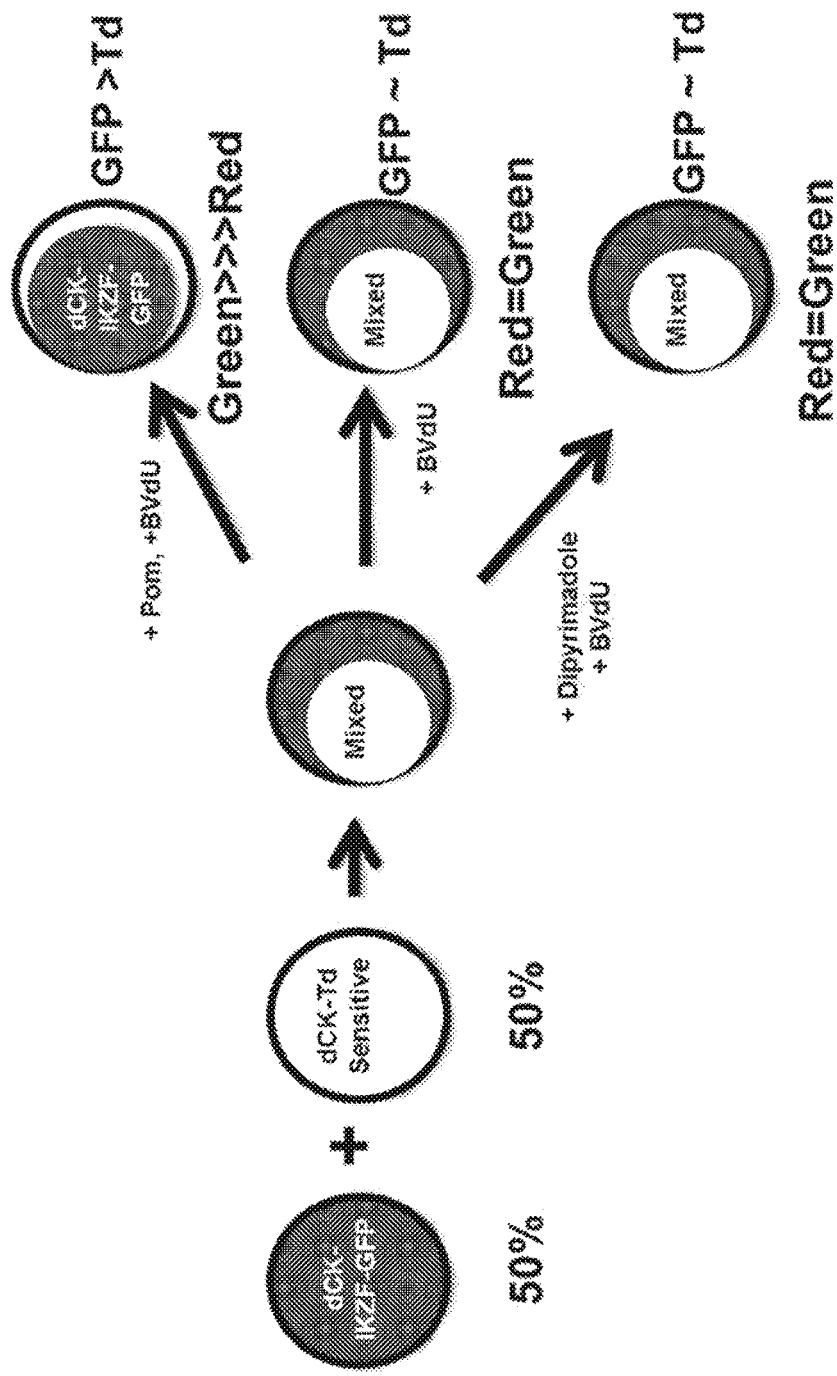
FIG. 27 is a schematic to illustrate a process for distinguishing true positive hits from assay positives in the same well.
Figure 28:
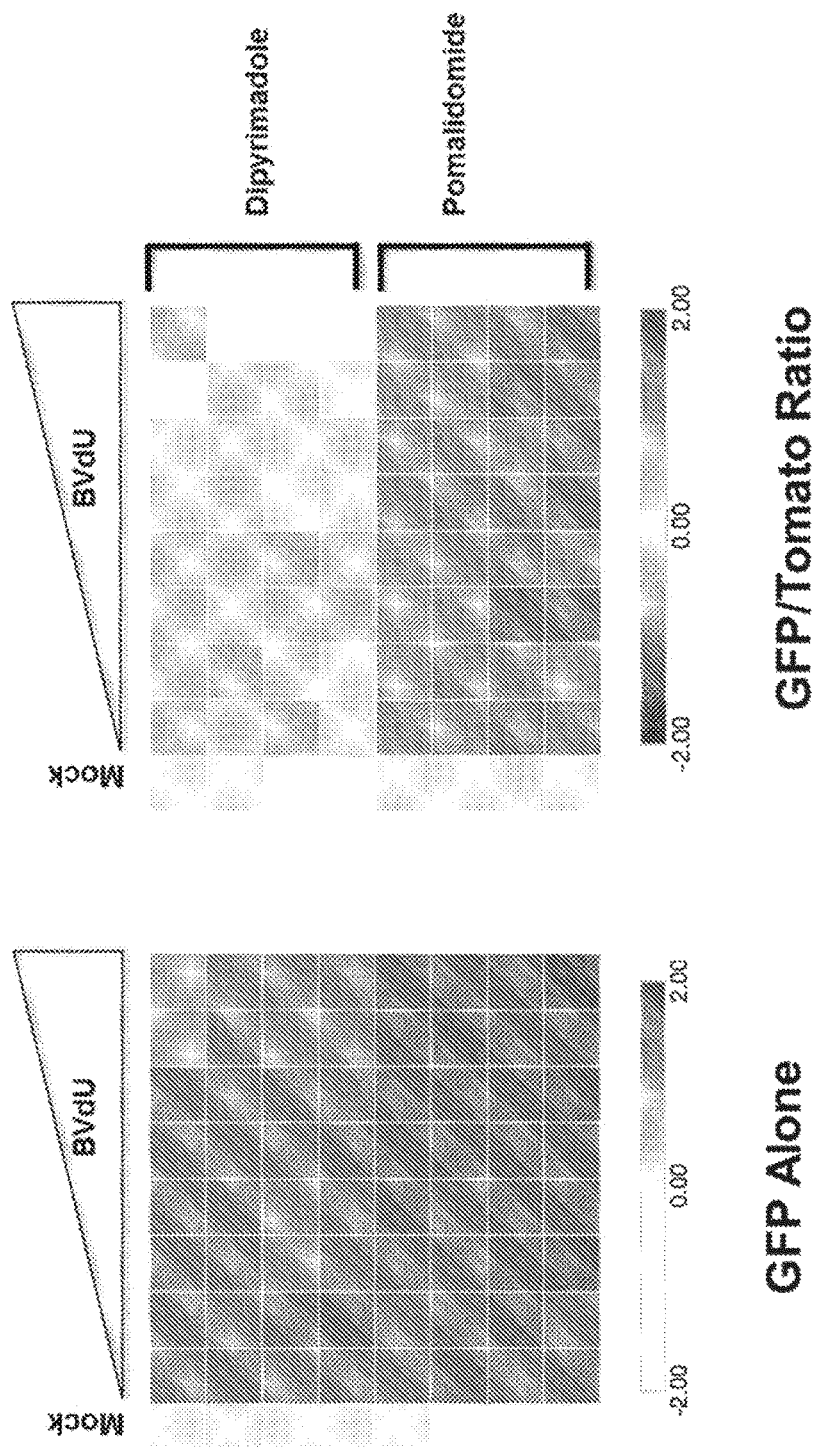
FIG. 28 depicts fluorescence measurements for GFP and GFP/Tomato ratio using wells having an assay positive (dipyridamole) and a true positive (Pomalidomide).

To determine whether the destabilization screen and a counter screen for assay positives could be performed simultaneously and on the same plate (thus reducing variability and cost), a 1:1 mixture of 293T stables expressing DCK-IRES-Tomato and DCK-IKZF1-IRES-GFP were plated together. FIG. 27 is a schematic to illustrate that if such a mixture is exposed to either DMSO (a simulated non-hit) or Dipyridamole (an "assay positive"), subsequent exposure to BVdU will not favor either component population, and the GFP/Tomato ratio will remain unchanged. However, exposure of the cells to Pomalidomide and subsequent BVdU exposure specifically rescues the DCK-IKZF1-IRES-GFP population and increases the GFP/Tomato ratio. This process was evaluated using Dipyridamole as an assay positive and Pomalidomide as a true positive (FIG. 28).

Figure 29:
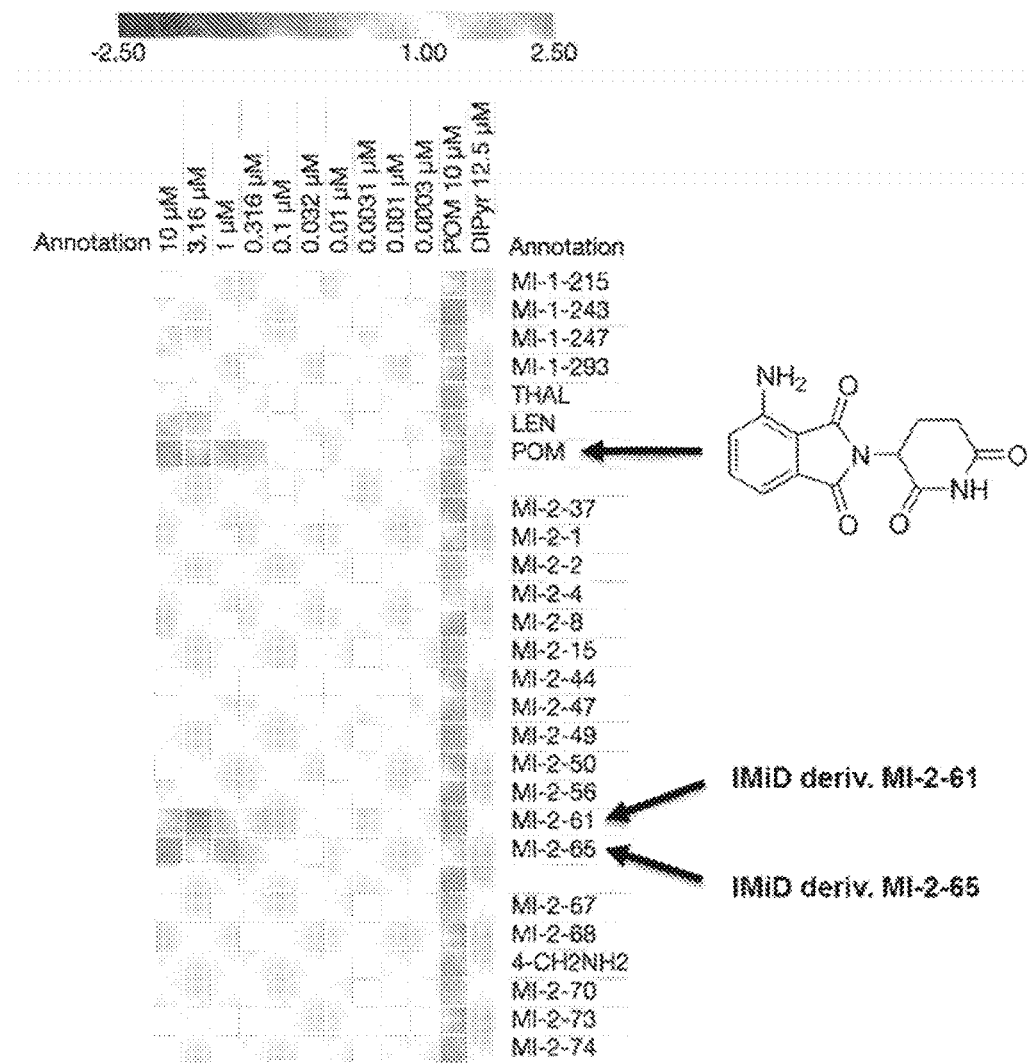
FIG. 29 depicts the results from an assay for distinguishing true positives from assay positives in the same well. Lenalidomide ("LEN"), Pomalidomide ("POM"), and a library of engineered IMiD derivatives were evaluated in the assay.

This assay was deployed in a proof of concept experiment with a small library of ~88 engineered IMiD derivatives and plated at 10 serial dilutions ranging from 10 µM to 300 pM. FIG. 29 illustrates the dose response for a number of compounds, including Pomalidomide and Lenalidomide, and further illustrates that most modifications to the IMiD backbone lead to a loss of activity of IKZF1 degradation. As shown, the assay was effective in identifying at least two potent IMiD derivatives as true positive hits (MI-2-61 and MI-2-65). The results demonstrate the utility of this assay in, for example, structure-activity relationship series to modify a desired compound to make it more or less potent.

Example 9

Expression and Localization of an Oncoprotein Fusion for Screening

Figures 30A, 30B:
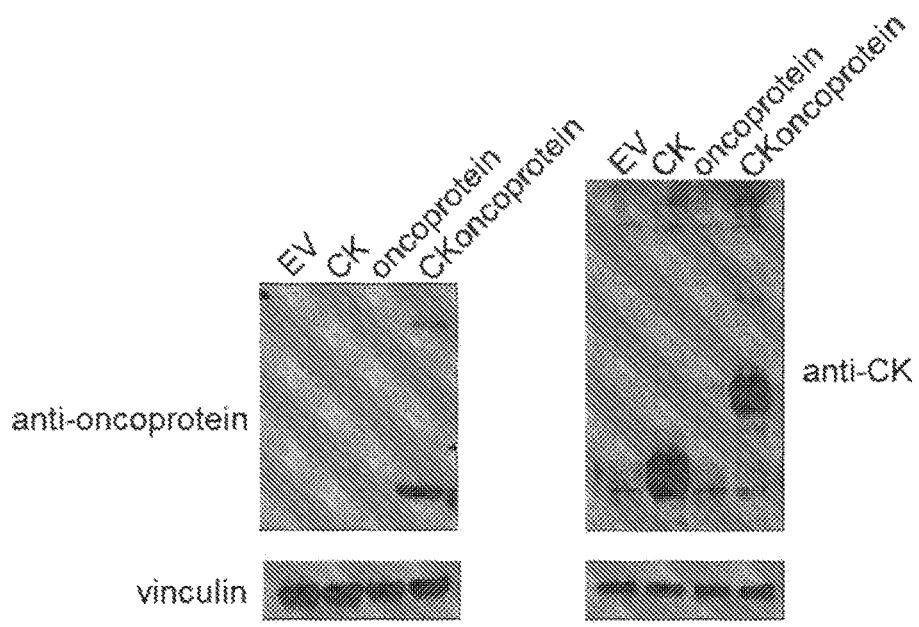
FIG. 30A and FIG. 30B depict results from experiments evaluating expression levels with a fusion protein having an oncoprotein other than an IKZF protein as a protein of interest.
Figure 30C:
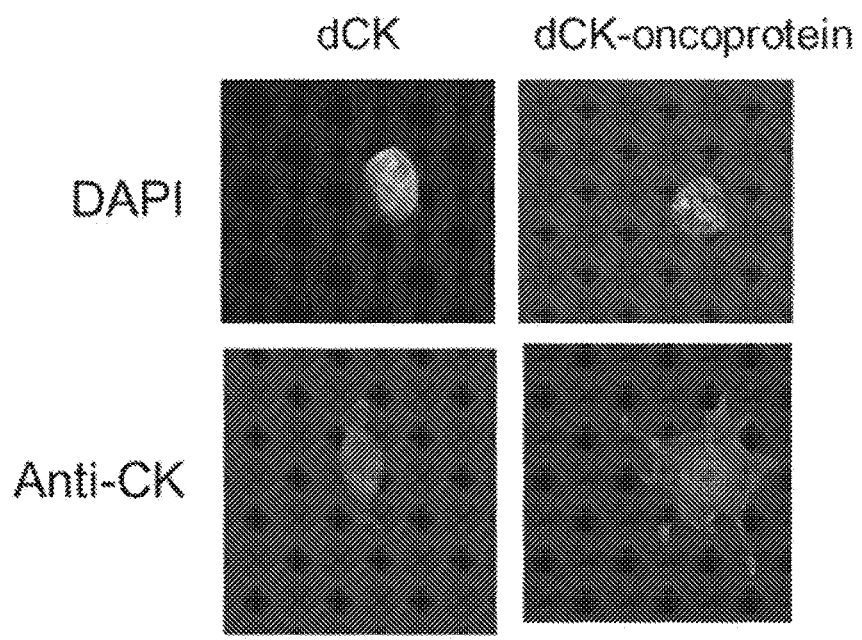
FIG. 30C depicts results from experiments evaluating localization of a fusion protein having an oncoprotein other than an IKZF protein as a protein of interest.
Figure 31:
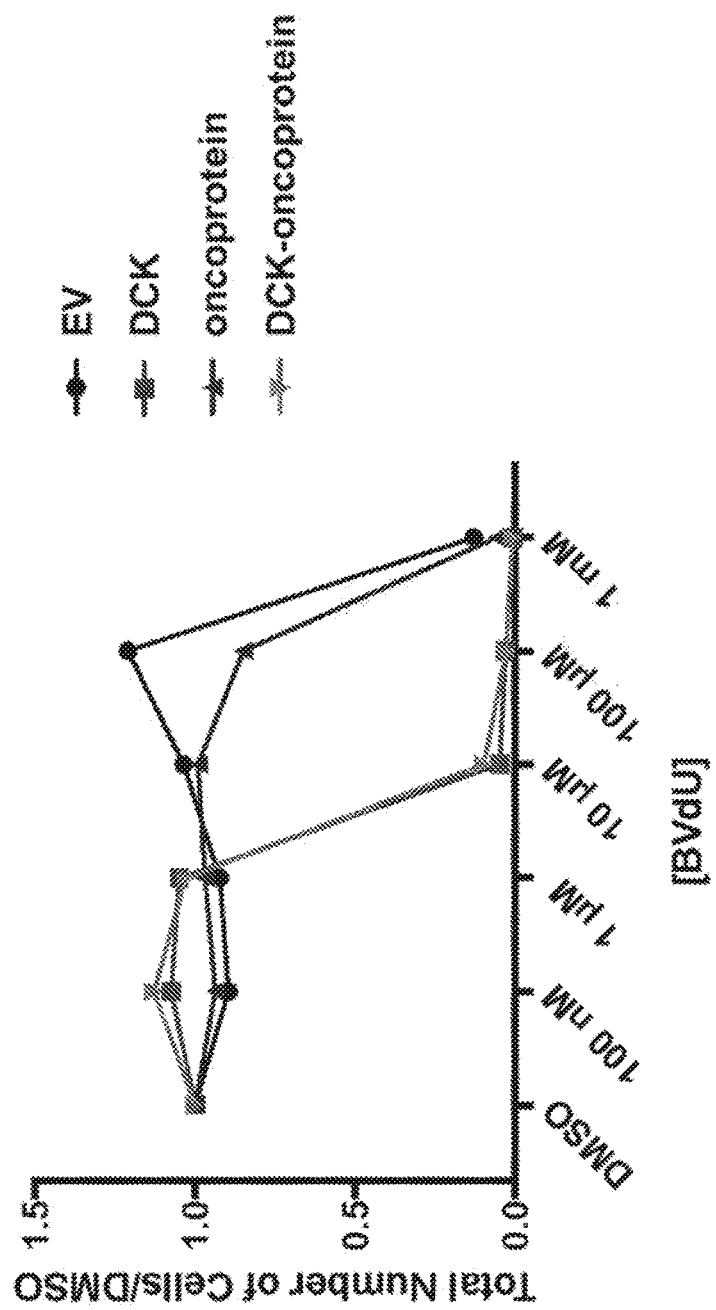
FIG. 31 depicts dose-response to BVdU, showing that expression of unfused dCK and dCK-oncoprotein sensitizes cells to BVdU.

As further proof of concept for positive selection using dCK fusion systems, an oncoprotein other than an IKZF protein was utilized as a protein of interest in a fusion construct for screening. Experiments with the dCK-oncoprotein fusion were conducted to evaluate expression levels (FIG. 30A and FIG. 30B) and localization (FIG. 30C). As shown in FIG. 31, expression of unfused dCK and dCK-oncoprotein sensitizes cells to BVdU.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be appreciated that embodiments described in this document using an open-ended transitional phrase (e.g., "comprising") are also contemplated, in alternative embodiments, as "consisting of" and "consisting essentially of" the feature described by the open-ended transitional phrase. For example, if the disclosure describes "a composition comprising A and B", the disclosure also contemplates the alternative embodiments "a composition consisting of A and B" and "a composition consisting essentially of A and B".

What is claimed is:

1. A method of identifying a test agent that destabilizes a protein of interest, the method comprising,
    providing cells expressing a recombinant fusion protein comprising a protein of interest and an enzyme, wherein the enzyme converts an exogenous substrate that is not toxic to the cells into a product that is toxic to the cells;
    contacting a first portion of the cells expressing the recombinant fusion protein with a test agent;
    culturing the first portion of the cells expressing the recombinant fusion protein in the presence of the exogenous substrate;
    culturing, separately from the first portion of cells expressing the recombinant fusion protein, a second portion of the cells expressing the recombinant fusion protein in the presence of the exogenous substrate, wherein the second portion of the cells expressing the recombinant fusion protein is not contacted with the test agent;
    determining a level of cell survival in each of the cultured portions, wherein a greater level of cell survival in the first portion compared to the second portion indicates that the test agent destabilizes either the protein of interest or the enzyme;
    further providing cells expressing a recombinant protein comprising the enzyme;
    culturing the cells expressing the recombinant protein comprising the enzyme in the presence of the exogenous substrate and in the presence or absence of the test agent that destabilizes either the protein of interest or the enzyme;
    determining the level of cell survival in the presence and absence of the test agent that destabilizes either the protein of interest or the enzyme, wherein the lack of a significantly greater difference in the level of cell survival in the presence of the test agent compared to the level of cell survival in the absence of the test agent indicates that the test agent destabilizes the protein of interest.

2. The method of claim 1, wherein the protein of interest is an oncoprotein.

3. The method of claim 2, wherein the oncoprotein is selected from the group consisting of MYC, Ikaros family zinc finger protein 1 (IKZF1), Ikaros family zinc finger protein 3 (IKZF3), Interferon regulatory factor 4, mutant p53, N-Ras, K-Ras, c-Fos, c-Jun, and estrogen receptor (ER).

4. The method of claim 1, wherein the protein of interest is a protein associated with neurodegeneration.

5. The method of claim 1, wherein the protein of interest is a prion or an amyloid protein.

6. The method of claim 1, wherein the enzyme is selected from the group consisting of deoxycytidine kinase, thymidylate kinase, thymidine kinase-guanylate kinase fusion, and FKBP-Caspase9 fusion.

7. The method of claim 1, wherein the exogenous substrate is a synthetic compound.

8. The method of claim 7, wherein the synthetic compound is a nucleoside analog.

9. The method of claim 8, wherein the nucleoside analog is selected from the group consisting of bromovinyl-deoxyuridine, azidothymidine (AZT), and Ganciclovir.

10. The method of claim 1, wherein the test agent is selected from the group consisting of a small organic molecule, an amino acid, a protein, a nucleoside, a nucleotide, a nucleic acid, or an analog or derivative thereof.

11. The method of claim 1, wherein the test agent is an immunomodulatory drug (IMiD).

12. The method of claim 11, wherein the IMiD is selected from the group consisting of thalidomide, lenalidomide, and pomalidomide.

13. The method of claim 1, wherein the test agent is an estrogen receptor antagonist.

14. The method of claim 13, wherein the estrogen receptor antagonist is Fulvestrant.

15. The method of claim 1, wherein the cells further express a reporter protein, and wherein determining the level of cell survival is based on the detection of the reporter protein signal.

16. The method of claim 15, wherein the reporter protein is a fluorescent protein or a bioluminescent protein.

17. A method of identifying a test agent that destabilizes a protein of interest, the method comprising,
    providing cells expressing a recombinant fusion protein comprising a protein of interest and an enzyme, wherein the enzyme converts an exogenous substrate that is not toxic to the cells into a product that is toxic to the cells;
    contacting the cells expressing the recombinant fusion protein with a library of test agents;
    culturing the cells expressing the recombinant fusion protein in the presence of the exogenous substrate;
    determining cell survival in the cultured cells expressing the recombinant fusion protein, wherein survival of a cell indicates that a test agent from the library of test agents destabilizes either the protein of interest or the enzyme;
    isolating the surviving cell;

further providing cells expressing a recombinant protein comprising the enzyme;

culturing the cells expressing the recombinant protein comprising the enzyme in the presence or absence of the test agent from the library of test agents that destabilizes either the protein of interest or the enzyme;

determining the level of cell survival in the presence and absence of the test agent that destabilizes either the protein of interest or the enzyme, wherein the lack of a significantly greater difference in the level of cell survival in the presence of the test agent compared to the level of cell survival in the absence of the test agent indicates that the test agent destabilizes the protein of interest.

18. A method of identifying a test agent that destabilizes a protein of interest, the method comprising, providing a mixture of cells comprising a first portion of cells expressing a recombinant fusion protein comprising a protein of interest and an enzyme and a second portion of cells expressing a recombinant protein comprising the enzyme, wherein the enzyme converts an exogenous substrate that is not toxic to the cells into a product that is toxic to the cells, wherein the recombinant fusion protein of the first portion of cells comprises a first reporter protein and the recombinant protein of the second portion of cells comprises a second reporter protein, and wherein the second reporter protein is different from the first reporter protein;

contacting the mixture of cells with a test agent;

culturing the mixture of cells in the presence of the exogenous substrate; and determining a level of cell survival for each of the portions in the cultured mixture, wherein a ratio of the number of cells in the first portion to the number of cells in the second portion in the cultured mixture greater than 1 indicates that the test agent destabilizes the protein of interest.

* * * * *